(12) United States Patent
Matasci et al.

(10) Patent No.: US 12,173,044 B2
(45) Date of Patent: Dec. 24, 2024

(54) EDB TARGETING IL-12 COMPOSITIONS

(71) Applicant: Philogen S.P.A., Siena (IT)

(72) Inventors: Mattia Matasci, Otelfingen (CH); Tiziano Ongaro, Otelfingen (CH); Alessandra Villa, Otelfingen (CH)

(73) Assignee: Philogen S.P.A., Siena (IT)

( * ) Notice: Subject to any disclaimer, the term of this patent is extended or adjusted under 35 U.S.C. 154(b) by 1128 days.

(21) Appl. No.: 16/968,445

(22) PCT Filed: Feb. 8, 2019

(86) PCT No.: PCT/EP2019/053136
§ 371 (c)(1),
(2) Date: Aug. 7, 2020

(87) PCT Pub. No.: WO2019/154986
PCT Pub. Date: Aug. 15, 2019

(65) Prior Publication Data
US 2020/0397915 A1 Dec. 24, 2020

(30) Foreign Application Priority Data

Feb. 9, 2018 (EP) .................................. 18156141
Jun. 22, 2018 (EP) .................................. 18179313

(51) Int. Cl.
| C07K 14/54 | (2006.01) |
| A61K 47/65 | (2017.01) |
| A61K 47/68 | (2017.01) |
| A61P 35/00 | (2006.01) |
| C07K 16/18 | (2006.01) |

(52) U.S. Cl.
CPC .......... *C07K 14/5434* (2013.01); *A61K 47/65* (2017.08); *A61K 47/6813* (2017.08); *A61P 35/00* (2018.01); *C07K 16/18* (2013.01)

(58) Field of Classification Search
None
See application file for complete search history.

(56) References Cited

U.S. PATENT DOCUMENTS 5,595,756 A * 1/1997 Bally .................... A61K 9/1272
264/4.1

FOREIGN PATENT DOCUMENTS

| WO | 0162298 A2 | 8/2001 |
| WO | 0162800 A1 | 8/2001 |
| WO | 03076469 A2 | 9/2003 |
| WO | 2006119897 A2 | 11/2006 |
| WO | 2011020783 A2 | 2/2011 |
| WO | 2013014149 A1 | 1/2013 |
| WO | 2017/062953 A1 | 4/2017 |
| WO | 2018153865 A1 | 8/2018 |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000,10:398-400) (Year: 2000).*
Ma (Modern Drug Discovery 2004, 7(6)) (Year: 2004).*
Sporn et al., "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
Hogenesch et al (J Control Release. Dec. 10, 2012; 164(2): 183-186.) (Year: 2012).*
Office Action, dated Nov. 9, 2022, issued in corresponding Columbian Patent Application No. NC2020/0009737.
Notification on the necessity of submission of supplementary materials, dated Aug. 24, 2022, issued in corresponding Eurasian Patent Application No. 202091752.
The Result of Stage I of Substantive Examination, dated Jun. 13, 2022, issued in corresponding Indonesian Patent Application No. P00202005772.
Written Opinion, dated Dec. 7, 2022, issued in corresponding Vietnamese Patent Application No. 1-2020-05134.
Marty, C. et al., "Cytotoxic targeting of F9 teratocarcinoma tumours with anti-ED-B fibronectin scFv antibody modified liposomes," British Journal of Cancer, vol. 87, 2002, pp. 106-112.
Office Action, dated Feb. 2, 2022, issued in corresponding Korean Patent Application No. 10-2021-7015607.
Official Action, dated Feb. 24, 2021, issued in corresponding Russian Application No. 2020127719, filed Feb. 8, 2019.
Federal Institute of Industrial Property (FIPS), Search Report, dated Feb. 20, 2021, issued in corresponding Russian Application No. 2020127719, filed Feb. 8, 2019.
Yujin Sun et al., "MRI of Breast Tumor Initiating Cells Using the Extra Domain-B of Fibronectin Targeting Nanoparticles," Theranostics, 2014, vol. 4, No. 8, pp. 845-857.
Australian Public Assessment Report for Ranibizumab, Oct. 14, 2014, pp. 1-44. https://www.tga.gov.au/sites/default/files/auspar-ranibizumab-141014.pdf.
Sylviane Muller et al., "Spliceosomal peptide P140 for immunotherapy of systemic lupus erythematosus: results of an early phase II clinical trial," Arthritis & Rheumatology, Dec. 2008, vol. 58, No. 12, pp. 3873-3883.
Chothia; Lesk, J. Mol. Biol., (1987), vol. 196, pp. 901-917.
Chothia et al., Nature, (1989), vol. 342, pp. 877-883.
Chothia et al., J. Mol. Biol., (1992), vol. 227, pp. 799-817.

(Continued)

*Primary Examiner* — Brian Gangle
*Assistant Examiner* — Andrea K Mccollum
(74) *Attorney, Agent, or Firm* — Kathleen D. Rigaut; Howson & Howson LLP

(57) ABSTRACT

The present invention relates to compositions comprising an interleukin-12 (IL-12) protein having a first and second subunit, an extra domain B (ED-B)-binding domain, and a linker between the IL-12 protein and the ED-B-binding domain.

13 Claims, 19 Drawing Sheets
Specification includes a Sequence Listing.

(56) References Cited

OTHER PUBLICATIONS

Al-Lazikani et al., J.Mol.Biol., (1997), vol. 273, pp. 927-748.
Maccallum et al., J. Mol. Biol., (1996), vol. 262, pp. 732-745.
Martin et al., Proc. Natl. Acad. Sci. USA, (1989), vol. 86, pp. 9268-9272.
Bowie et al., Science, (1990), vol. 247, pp. 306-1310.
Morrison et al., Proc. Natl. Acad. Sci. USA, (1984), vol. 81, pp. 6851-6855.
Morrison; Oi, Adv. Immunol., (1988), vol. 44, pp. 65-92.
Verhoeyen et al., Science, (1988), vol. 239, pp. 1534-1536.
Padlan, Molec. Immun., (1991), vol. 28, pp. 489-498.
Padlan, Molec. Immun., (1994), vol. 31, No. 3, pp. 169-217.
Batzer et al., Nucleic Acid Res., (1991), vol. 19, p. 5081.
Ohtsuka et al., J. Biol. Chem., (1985), vol. 260, pp. 2605-2608.
Rossolini et al., Mol. Cell. Probes, (1994), vol. 8, pp. 91-98.
Car et al., Toxicologic Pathology, (1999), vol. 27, No. 1, pp. 58-63.
Chen et al., Adv Drug Deliv Rev., (2013), vol. 65, No. 10, pp. 1357-1369.
International Search Report for PCT/EP2019/053136 mailed on May 17, 2019.
Gafner V, Trachsel E, Neri D: "An engineered antibody-interleukin-12 fusion protein with enhanced tumor vascular targeting properties", International Journal of Cancer, Nov. 1, 2006 John Wiley & Sons, Inc, US, vol. 119, Nr: 9, pp. 2205-2212.
Tiziano Ongaro, et al: "A novei anti-cancer L 19-interleukin-12 fusion protein with an optimized peptide linker efficiently localizes in vivo at the site of tumors", Journal of Biotechnology, Feb. 1, 2019 Elsevier, Amsterdam, NL, vol. 291, pp. 17-25.
Johnson et al., "Kabat Database and its applications: future directions", Nucleic Acids Res., (2001), vol. 29, pp. 205-206.
Ruiz et al., "IMGT, teh international ImMunoGeneTics database", Nucleic Acids Res., (2000), vol. 28, pp. 219-221.
Lefranc, M.P., "IMGT, the international ImMunoGeneTics database", Nucleic Acids Res., (2001), vol. 29, pp. 207-209.
Knappik et al., "Fully Synthetic Human Combinatorial Antibody Libraries (HuCAL) Based on Modular Consensus Frameworks and CDRs Randomized with Trinucleotides", J. Mol. Biol., (2000), vol. 296, pp. 57-86.
Tarli et al., "A High-Affinity Human Antibody That Targets Tumoral Blood Vessels", Blood, (1999), vol. 94, No. 1, pp. 192-198.
Halin, C. et al., "Enhancement of the antitumor activity of interleukin-12 by targeted delivery to neovasculature," Nature Biotechnology, vol. 20, No. 3, 2002, pp. 264-269.
Office Action, dated May 5, 2023, issued in corresponding ROC (Taiwan) Patent Application No. 108104259.
First Office Action, dated Sep. 23, 2023, issued in corresponding Chinese Patent Application No. 201980012247.6.

\* cited by examiner

| clone (SEQ ID NO) | PxxID - linker sequence (nucleotide) | PxxID - linker sequence (aminoacid) | Production yields |
|---|---|---|---|
| AKKA5 (18/9) | ...GGAGGGGGAGCTAAAGGTGGCGGTGGCAAGGCAGGCGGAGGCAAGGGAGGAGGAAGT... | ...GGGGAKGGGGKAGGGKGGGS... | 4.6 mg/L |
| AP7 (19/15) | ...GCACCAGCACCAGCACCAGGCACCACCAGCACCAGCACCAGGCACCA... | ...APAPAPAPAPAPAPAP... | 4.7 mg/L |
| DD5 (20/10) | ...GGAGGTGGGGGTGATGGTGGGGGAGGTGATGGCGGGAGGTGGTGGTGT... | ...GGGGDGGGGDGGGGS... | 5.0 mg/L |
| AP6 (21/14) | ...GCACCAGCACAGCAGCACCAGCACCAGGCACCAGCACCA... | ...APAPAPAPAPAP... | 3.5 mg/L |
| (G4S)3 (22/11) | ...GGTGGAGGCGGGTCAGGCGGAGGGGGTTCTGGCGGTGGCGGATCG... | ...GGGGSGGGGSGGGGS... | 3.5 mg/L |
| SE5 (23/12) | ...GGTGGAGGGTGGGTCCGGAGGCGGAGGCGGAGGCTGGAGGTGGCGGGAG... | ...GGGGSGGGGEGGGGS... | 4.4 mg/L |
| Alpha3 (24/13) | ...GCAGAGGCAGCCAAAGAAGCAGCAGCAAAGGAAGCGGCAGCAAAAGCA... | ...AEAAAKEAAARKEAAAKA... | 4.5 mg/L |
| SAD (25/4) | ...GGGGTCTGCAGCAGCGGCGGAGATCATCAGCTGCGGGAAGTTGAGCAGGSAGSAG... | ...GSADGSSAAGGSSDAG... | 9.0 mg/L |

Fig. 1A

[prior art for illustrative purposes]

[prior art for illustrative purposes]

SEQUENCE LISTING

<160> NUMBER OF SEQ ID NOS: 36

<210> SEQ ID NO 1
<211> LENGTH: 306
<212> TYPE: PRT
<213> ORGANISM: Homo sapiens

<400> SEQUENCE: 1

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 2
<211> LENGTH: 15
<212> TYPE: PRT
<213> ORGANISM: artificial sequence
<220> FEATURE:
<223> OTHER INFORMATION: linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 197
<212> TYPE: PRT
<213> ORGANISM: Homo sapiens

<400> SEQUENCE: 3

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu

```
                50                  55                  60
Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
                180                 185                 190

Tyr Leu Asn Ala Ser
            195

<210> SEQ ID NO 4
<211> LENGTH: 15
<212> TYPE: PRT
<213> ORGANISM: artificial sequence
<220> FEATURE:
<223> OTHER INFORMATION: linker

<400> SEQUENCE: 4

Gly Ser Ala Asp Gly Gly Ser Ser Ala Gly Gly Ser Asp Ala Gly
1               5                   10                  15

<210> SEQ ID NO 5
<211> LENGTH: 108
<212> TYPE: PRT
<213> ORGANISM: artificial sequence
<220> FEATURE:
<223> OTHER INFORMATION: antibody sequence (variable domain)

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 6
<211> LENGTH: 5
<212> TYPE: PRT
<213> ORGANISM: artificial sequence
<220> FEATURE:
```

```
<223> OTHER INFORMATION: linker

<400> SEQUENCE: 6

Gly Ser Ser Gly Gly
1               5

<210> SEQ ID NO 7
<211> LENGTH: 116
<212> TYPE: PRT
<213> ORGANISM: artificial sequence
<220> FEATURE:
<223> OTHER INFORMATION: antibody sequence (variable domain)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 8
<211> LENGTH: 15
<212> TYPE: PRT
<213> ORGANISM: artificial sequence
<220> FEATURE:
<223> OTHER INFORMATION: linker

<400> SEQUENCE: 8

Ser Ser Ser Ser Gly Ser Ser Ser Gly Ser Ser Ser Ser Gly
1               5                   10                  15

<210> SEQ ID NO 9
<211> LENGTH: 15
<212> TYPE: PRT
<213> ORGANISM: artificial sequence
<220> FEATURE:
<223> OTHER INFORMATION: linker

<400> SEQUENCE: 9

Gly Gly Gly Ala Lys Gly Gly Gly Lys Ala Gly Gly Gly Ser
1               5                   10                  15

<210> SEQ ID NO 10
<211> LENGTH: 15
<212> TYPE: PRT
<213> ORGANISM: artificial sequence
<220> FEATURE:
<223> OTHER INFORMATION: linker

<400> SEQUENCE: 10

Gly Gly Gly Gly Asp Gly Gly Gly Asp Gly Gly Gly Ser
1               5                   10                  15
```

<210> SEQ ID NO 11
<211> LENGTH: 15
<212> TYPE: PRT
<213> ORGANISM: artificial sequence
<220> FEATURE:
<223> OTHER INFORMATION: linker

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 15
<212> TYPE: PRT
<213> ORGANISM: artificial sequence
<220> FEATURE:
<223> OTHER INFORMATION: linker

<400> SEQUENCE: 12

Gly Gly Gly Gly Ser Gly Gly Gly Gly Glu Gly Gly Gly Gly Ser
1               5                   10                  15

<210> SEQ ID NO 13
<211> LENGTH: 17
<212> TYPE: PRT
<213> ORGANISM: artificial sequence
<220> FEATURE:
<223> OTHER INFORMATION: linker

<400> SEQUENCE: 13

Ala Glu Ala Ala Ala Lys Glu Ala Ala Ala Lys Glu Ala Ala Ala Lys
1               5                   10                  15
Ala

<210> SEQ ID NO 14
<211> LENGTH: 12
<212> TYPE: PRT
<213> ORGANISM: artificial sequence
<220> FEATURE:
<223> OTHER INFORMATION: linker

<400> SEQUENCE: 14

Ala Pro Ala Pro Ala Pro Ala Pro Ala Pro Ala Pro
1               5                   10

<210> SEQ ID NO 15
<211> LENGTH: 14
<212> TYPE: PRT
<213> ORGANISM: artificial sequence
<220> FEATURE:
<223> OTHER INFORMATION: linker

<400> SEQUENCE: 15

Ala Pro Ala Pro Ala Pro Ala Pro Ala Pro Ala Pro Ala Pro
1               5                   10

<210> SEQ ID NO 16
<211> LENGTH: 1006
<212> TYPE: PRT
<213> ORGANISM: artificial sequence
<220> FEATURE:
<223> OTHER INFORMATION: Immunoconjugate sequence

<400> SEQUENCE: 16

Ile Trp Glu Leu Lys Lys Asp Val Tyr Val Val Glu Leu Asp Trp Tyr

-continued

```
1               5                   10                  15
Pro Asp Ala Pro Gly Glu Met Val Val Leu Thr Cys Asp Thr Pro Glu
                20                  25                  30
Glu Asp Gly Ile Thr Trp Thr Leu Asp Gln Ser Ser Glu Val Leu Gly
                35                  40                  45
Ser Gly Lys Thr Leu Thr Ile Gln Val Lys Glu Phe Gly Asp Ala Gly
    50                  55                  60
Gln Tyr Thr Cys His Lys Gly Glu Val Leu Ser His Ser Leu Leu
65                  70                  75                  80
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
                100                 105                 110
Asn Tyr Ser Gly Arg Phe Thr Cys Trp Trp Leu Thr Thr Ile Ser Thr
                115                 120                 125
Asp Leu Thr Phe Ser Val Lys Ser Ser Arg Gly Ser Ser Asp Pro Gln
                130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
                180                 185                 190
Val His Lys Leu Lys Tyr Glu Asn Tyr Thr Ser Ser Phe Phe Ile Arg
                195                 200                 205
Asp Ile Ile Lys Pro Asp Pro Pro Lys Asn Leu Gln Leu Lys Pro Leu
                210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
                260                 265                 270
Ser Ala Thr Val Ile Cys Arg Lys Asn Ala Ser Ile Ser Val Arg Ala
                275                 280                 285
Gln Asp Arg Tyr Tyr Ser Ser Trp Ser Glu Trp Ala Ser Val Pro
                290                 295                 300
Cys Ser Gly Gly Gly Ser Gly Gly Gly Ser Gly Gly Gly Gly
305                 310                 315                 320
Ser Arg Asn Leu Pro Val Ala Thr Pro Asp Pro Gly Met Phe Pro Cys
                325                 330                 335
Leu His His Ser Gln Asn Leu Leu Arg Ala Val Ser Asn Met Leu Gln
                340                 345                 350
Lys Ala Arg Gln Thr Leu Glu Phe Tyr Pro Cys Thr Ser Glu Glu Ile
                355                 360                 365
Asp His Glu Asp Ile Thr Lys Asp Lys Thr Ser Thr Val Glu Ala Cys
                370                 375                 380
Leu Pro Leu Glu Leu Thr Lys Asn Glu Ser Cys Leu Asn Ser Arg Glu
385                 390                 395                 400
Thr Ser Phe Ile Thr Asn Gly Ser Cys Leu Ala Ser Arg Lys Thr Ser
                405                 410                 415
Phe Met Met Ala Leu Cys Leu Ser Ser Ile Tyr Glu Asp Leu Lys Met
                420                 425                 430
```

```
Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Ser Ala Asp Gly Gly Ser Ser Ala Gly
        515                 520                 525

Gly Ser Asp Ala Gly Glu Val Gln Leu Leu Glu Ser Gly Gly Gly Leu
        530                 535                 540

Val Gln Pro Gly Gly Ser Leu Arg Leu Ser Cys Ala Ala Ser Gly Phe
545                 550                 555                 560

Thr Phe Ser Ser Phe Ser Met Ser Trp Val Arg Gln Ala Pro Gly Lys
                565                 570                 575

Gly Leu Glu Trp Val Ser Ser Ile Ser Gly Ser Ser Gly Thr Thr Tyr
            580                 585                 590

Tyr Ala Asp Ser Val Lys Gly Arg Phe Thr Ile Ser Arg Asp Asn Ser
        595                 600                 605

Lys Asn Thr Leu Tyr Leu Gln Met Asn Ser Leu Arg Ala Glu Asp Thr
        610                 615                 620

Ala Val Tyr Tyr Cys Ala Lys Pro Phe Pro Tyr Phe Asp Tyr Trp Gly
625                 630                 635                 640

Gln Gly Thr Leu Val Thr Val Ser Ser Gly Ser Gly Gly Glu Ile
                645                 650                 655

Val Leu Thr Gln Ser Pro Gly Thr Leu Ser Leu Ser Pro Gly Glu Arg
            660                 665                 670

Ala Thr Leu Ser Cys Arg Ala Ser Gln Ser Val Ser Ser Ser Phe Leu
        675                 680                 685

Ala Trp Tyr Gln Gln Lys Pro Gly Gln Ala Pro Arg Leu Leu Ile Tyr
        690                 695                 700

Tyr Ala Ser Ser Arg Ala Thr Gly Ile Pro Asp Arg Phe Ser Gly Ser
705                 710                 715                 720

Gly Ser Gly Thr Asp Phe Thr Leu Thr Ile Ser Arg Leu Glu Pro Glu
                725                 730                 735

Asp Phe Ala Val Tyr Tyr Cys Gln Gln Thr Gly Arg Ile Pro Pro Thr
            740                 745                 750

Phe Gly Gln Gly Thr Lys Val Glu Ile Lys Ser Ser Ser Ser Gly Ser
        755                 760                 765

Ser Ser Ser Gly Ser Ser Ser Gly Glu Val Gln Leu Leu Glu Ser
        770                 775                 780

Gly Gly Gly Leu Val Gln Pro Gly Gly Ser Leu Arg Leu Ser Cys Ala
785                 790                 795                 800

Ala Ser Gly Phe Thr Phe Ser Ser Phe Ser Met Ser Trp Val Arg Gln
                805                 810                 815

Ala Pro Gly Lys Gly Leu Glu Trp Val Ser Ser Ile Ser Gly Ser Ser
            820                 825                 830

Gly Thr Thr Tyr Tyr Ala Asp Ser Val Lys Gly Arg Phe Thr Ile Ser
        835                 840                 845
```

```
Arg Asp Asn Ser Lys Asn Thr Leu Tyr Leu Gln Met Asn Ser Leu Arg
    850                 855                 860

Ala Glu Asp Thr Ala Val Tyr Tyr Cys Ala Lys Pro Phe Pro Tyr Phe
865                 870                 875                 880

Asp Tyr Trp Gly Gln Gly Thr Leu Val Thr Val Ser Ser Gly Ser Ser
                885                 890                 895

Gly Gly Glu Ile Val Leu Thr Gln Ser Pro Gly Thr Leu Ser Leu Ser
            900                 905                 910

Pro Gly Glu Arg Ala Thr Leu Ser Cys Arg Ala Ser Gln Ser Val Ser
            915                 920                 925

Ser Ser Phe Leu Ala Trp Tyr Gln Gln Lys Pro Gly Gln Ala Pro Arg
930                 935                 940

Leu Leu Ile Tyr Tyr Ala Ser Ser Arg Ala Thr Gly Ile Pro Asp Arg
945                 950                 955                 960

Phe Ser Gly Ser Gly Ser Gly Thr Asp Phe Thr Leu Thr Ile Ser Arg
                965                 970                 975

Leu Glu Pro Glu Asp Phe Ala Val Tyr Tyr Cys Gln Gln Thr Gly Arg
            980                 985                 990

Ile Pro Pro Thr Phe Gly Gln Gly  Thr Lys Val Glu Ile  Lys
            995                 1000                1005

<210> SEQ ID NO 17
<211> LENGTH: 999
<212> TYPE: PRT
<213> ORGANISM: artificial sequence
<220> FEATURE:
<223> OTHER INFORMATION: Immunoconjugate sequence

<400> SEQUENCE: 17

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
                20                  25                  30

Glu Asp Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
                100                 105                 110

Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
    195                 200                 205
```

-continued

```
Ile Lys Pro Asp Pro Pro Lys Asn Leu Gln Met Arg Pro Leu Lys Asn
210                 215                 220
Ser Gln Val Glu Val Ser Trp Glu Tyr Pro Asp Ser Trp Ser Thr Pro
225                 230                 235                 240
His Ser Tyr Phe Ser Leu Lys Phe Phe Val Arg Ile Gln Arg Lys Lys
                245                 250                 255
Glu Lys Met Lys Glu Thr Glu Glu Gly Cys Asn Gln Lys Gly Ala Phe
            260                 265                 270
Leu Val Glu Arg Thr Ser Thr Glu Val Gln Cys Lys Gly Gly Asn Val
        275                 280                 285
Cys Val Gln Ala Gln Asp Arg Tyr Tyr Asn Ser Ser Cys Ser Lys Trp
290                 295                 300
Ala Cys Val Pro Cys Arg Val Arg Ser Gly Gly Gly Ser Gly Gly
305                 310                 315                 320
Gly Gly Ser Gly Gly Gly Gly Ser Arg Val Ile Pro Val Ser Gly Pro
                325                 330                 335
Ala Arg Cys Leu Ser Gln Ser Arg Asn Leu Leu Lys Thr Thr Asp Asp
            340                 345                 350
Met Val Lys Thr Ala Arg Glu Lys Leu Lys His Tyr Ser Cys Thr Ala
        355                 360                 365
Glu Asp Ile Asp His Glu Asp Ile Thr Arg Asp Gln Thr Ser Thr Leu
370                 375                 380
Lys Thr Cys Leu Pro Leu Glu Leu His Lys Asn Glu Ser Cys Leu Ala
385                 390                 395                 400
Thr Arg Glu Thr Ser Ser Thr Thr Arg Gly Ser Cys Leu Pro Pro Gln
                405                 410                 415
Lys Thr Ser Leu Met Met Thr Leu Cys Leu Gly Ser Ile Tyr Glu Asp
            420                 425                 430
Leu Lys Met Tyr Gln Thr Glu Phe Gln Ala Ile Asn Ala Ala Leu Gln
        435                 440                 445
Asn His Asn His Gln Gln Ile Ile Leu Asp Lys Gly Met Leu Val Ala
450                 455                 460
Ile Asp Glu Leu Met Gln Ser Leu Asn His Asn Gly Glu Thr Leu Arg
465                 470                 475                 480
Gln Lys Pro Pro Val Gly Glu Ala Asp Pro Tyr Arg Val Lys Met Lys
                485                 490                 495
Leu Cys Ile Leu Leu His Ala Phe Ser Thr Arg Val Val Thr Ile Asn
            500                 505                 510
Arg Val Met Gly Tyr Leu Ser Ser Ala Gly Ser Ala Asp Gly Glu Val
        515                 520                 525
Gln Leu Leu Glu Ser Gly Gly Gly Leu Val Gln Pro Gly Gly Ser Leu
530                 535                 540
Arg Leu Ser Cys Ala Ala Ser Gly Phe Thr Phe Ser Ser Phe Ser Met
545                 550                 555                 560
Ser Trp Val Arg Gln Ala Pro Gly Lys Gly Leu Glu Trp Val Ser Ser
                565                 570                 575
Ile Ser Gly Ser Ser Gly Thr Thr Tyr Tyr Ala Asp Ser Val Lys Gly
            580                 585                 590
Arg Phe Thr Ile Ser Arg Asp Asn Ser Lys Asn Thr Leu Tyr Leu Gln
        595                 600                 605
Met Asn Ser Leu Arg Ala Glu Asp Thr Ala Val Tyr Tyr Cys Ala Lys
610                 615                 620
Pro Phe Pro Tyr Phe Asp Tyr Trp Gly Gln Gly Thr Leu Val Thr Val
```

```
              625                 630                 635                 640
    Ser Ser Gly Ser Ser Gly Gly Glu Ile Val Leu Thr Gln Ser Pro Gly
                    645                 650                 655

Thr Leu Ser Leu Ser Pro Gly Glu Arg Ala Thr Leu Ser Cys Arg Ala
                    660                 665                 670

Ser Gln Ser Val Ser Ser Phe Leu Ala Trp Tyr Gln Gln Lys Pro
                675                 680                 685

Gly Gln Ala Pro Arg Leu Leu Ile Tyr Tyr Ala Ser Ser Arg Ala Thr
            690                 695                 700

Gly Ile Pro Asp Arg Phe Ser Gly Ser Gly Ser Gly Thr Asp Phe Thr
    705                 710                 715                 720

Leu Thr Ile Ser Arg Leu Glu Pro Glu Asp Phe Ala Val Tyr Tyr Cys
                    725                 730                 735

Gln Gln Thr Gly Arg Ile Pro Pro Thr Phe Gly Gln Gly Thr Lys Val
                    740                 745                 750

Glu Ile Lys Ser Ser Ser Ser Gly Ser Ser Ser Gly Ser Ser Ser
                755                 760                 765

Ser Gly Glu Val Gln Leu Leu Glu Ser Gly Gly Gly Leu Val Gln Pro
        770                 775                 780

Gly Gly Ser Leu Arg Leu Ser Cys Ala Ala Ser Gly Phe Thr Phe Ser
    785                 790                 795                 800

Ser Phe Ser Met Ser Trp Val Arg Gln Ala Pro Gly Lys Gly Leu Glu
                    805                 810                 815

Trp Val Ser Ser Ile Ser Gly Ser Ser Gly Thr Thr Tyr Tyr Ala Asp
                    820                 825                 830

Ser Val Lys Gly Arg Phe Thr Ile Ser Arg Asp Asn Ser Lys Asn Thr
                835                 840                 845

Leu Tyr Leu Gln Met Asn Ser Leu Arg Ala Glu Asp Thr Ala Val Tyr
            850                 855                 860

Tyr Cys Ala Lys Pro Phe Pro Tyr Phe Asp Tyr Trp Gly Gln Gly Thr
    865                 870                 875                 880

Leu Val Thr Val Ser Ser Gly Ser Ser Gly Gly Glu Ile Val Leu Thr
                    885                 890                 895

Gln Ser Pro Gly Thr Leu Ser Leu Ser Pro Gly Glu Arg Ala Thr Leu
                    900                 905                 910

Ser Cys Arg Ala Ser Gln Ser Val Ser Ser Phe Leu Ala Trp Tyr
                915                 920                 925

Gln Gln Lys Pro Gly Gln Ala Pro Arg Leu Leu Ile Tyr Tyr Ala Ser
            930                 935                 940

Ser Arg Ala Thr Gly Ile Pro Asp Arg Phe Ser Gly Ser Gly Ser Gly
    945                 950                 955                 960

Thr Asp Phe Thr Leu Thr Ile Ser Arg Leu Glu Pro Glu Asp Phe Ala
                    965                 970                 975

Val Tyr Tyr Cys Gln Gln Thr Gly Arg Ile Pro Pro Thr Phe Gly Gln
                    980                 985                 990

Gly Thr Lys Val Glu Ile Lys
                995

<210> SEQ ID NO 18
<211> LENGTH: 45
<212> TYPE: PRT
<213> ORGANISM: artificial sequence
<220> FEATURE:
<223> OTHER INFORMATION: linker
```

<400> SEQUENCE: 18

Gly Gly Ala Gly Gly Gly Gly Ala Gly Cys Thr Ala Ala Ala Gly
1               5                   10                  15

Gly Thr Gly Gly Cys Gly Gly Thr Gly Gly Cys Ala Ala Gly Gly Cys
                20                  25                  30

Ala Gly Gly Gly Gly Ala Gly Gly Gly Ala Gly Thr
                35                  40                  45

<210> SEQ ID NO 19
<211> LENGTH: 42
<212> TYPE: DNA
<213> ORGANISM: artificial sequence
<220> FEATURE:
<223> OTHER INFORMATION: linker

<400> SEQUENCE: 19
gcaccagcac cagcaccagc accagcacca gcaccagcac ca                          42

<210> SEQ ID NO 20
<211> LENGTH: 45
<212> TYPE: DNA
<213> ORGANISM: artificial sequence
<220> FEATURE:
<223> OTHER INFORMATION: linker

<400> SEQUENCE: 20
ggaggtgggg gtgatggtgg gggaggtgac ggcggaggtg ggtct                       45

<210> SEQ ID NO 21
<211> LENGTH: 36
<212> TYPE: DNA
<213> ORGANISM: artificial sequence
<220> FEATURE:
<223> OTHER INFORMATION: linker

<400> SEQUENCE: 21
gcaccagcac cagcaccagc accagcacca gcacca                                 36

<210> SEQ ID NO 22
<211> LENGTH: 45
<212> TYPE: DNA
<213> ORGANISM: artificial sequence
<220> FEATURE:
<223> OTHER INFORMATION: linker

<400> SEQUENCE: 22
ggtggaggcg ggtcaggcgg aggggggttct ggcggtggcg gatcg                      45

<210> SEQ ID NO 23
<211> LENGTH: 45
<212> TYPE: DNA
<213> ORGANISM: artificial sequence
<220> FEATURE:
<223> OTHER INFORMATION: linker

<400> SEQUENCE: 23
ggtgggggtg ggtccggagg cggaggcgaa ggcggaggtg ggtcg                       45

<210> SEQ ID NO 24
<211> LENGTH: 51
<212> TYPE: DNA
<213> ORGANISM: artificial sequence
<220> FEATURE:
<223> OTHER INFORMATION: linker -continued

<400> SEQUENCE: 24
gcagaagcag cagcaaaaga agcagcagca aaagaagcag cagcaaaagc a          51

<210> SEQ ID NO 25
<211> LENGTH: 45
<212> TYPE: DNA
<213> ORGANISM: artificial sequence
<220> FEATURE:
<223> OTHER INFORMATION: linker

<400> SEQUENCE: 25
gggtctgcag acggcggatc atcagctggg ggaagtgacg cagga                45

<210> SEQ ID NO 26
<211> LENGTH: 6
<212> TYPE: PRT
<213> ORGANISM: artificial sequence
<220> FEATURE:
<223> OTHER INFORMATION: linker

<400> SEQUENCE: 26

Gly Ser Ala Asp Gly Gly
1               5

<210> SEQ ID NO 27
<211> LENGTH: 997
<212> TYPE: PRT
<213> ORGANISM: artificial sequence
<220> FEATURE:
<223> OTHER INFORMATION: Immunoconjugate sequence

<400> SEQUENCE: 27

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu

```
              210                 215                 220
Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                    245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
            290                 295                 300

Cys Ser Gly Gly Gly Ser Gly Gly Gly Ser Gly Gly Gly Gly
305                 310                 315                 320

Ser Arg Asn Leu Pro Val Ala Thr Pro Asp Pro Gly Met Phe Pro Cys
                    325                 330                 335

Leu His His Ser Gln Asn Leu Leu Arg Ala Val Ser Asn Met Leu Gln
                340                  345                 350

Lys Ala Arg Gln Thr Leu Glu Phe Tyr Pro Cys Thr Ser Glu Glu Ile
            355                 360                 365

Asp His Glu Asp Ile Thr Lys Asp Lys Thr Ser Thr Val Glu Ala Cys
370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                    405                 410                 415

Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
            435                 440                 445

Lys Arg Gln Ile Phe Leu Asp Gln Asn Met Leu Ala Val Ile Asp Glu
450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                    485                 490                 495

Leu Leu His Ala Phe Arg Ile Arg Ala Val Thr Ile Asp Arg Val Met
                500                 505                 510

Ser Tyr Leu Asn Ala Ser Gly Ser Ala Asp Gly Gly Glu Val Gln Leu
            515                 520                 525

Leu Glu Ser Gly Gly Gly Leu Val Gln Pro Gly Gly Ser Leu Arg Leu
530                 535                 540

Ser Cys Ala Ala Ser Gly Phe Thr Phe Ser Ser Phe Ser Met Ser Trp
545                 550                 555                 560

Val Arg Gln Ala Pro Gly Lys Gly Leu Glu Trp Val Ser Ser Ile Ser
                    565                 570                 575

Gly Ser Ser Gly Thr Thr Tyr Tyr Ala Asp Ser Val Lys Gly Arg Phe
                580                 585                 590

Thr Ile Ser Arg Asp Asn Ser Lys Asn Thr Leu Tyr Leu Gln Met Asn
            595                 600                 605

Ser Leu Arg Ala Glu Asp Thr Ala Val Tyr Tyr Cys Ala Lys Pro Phe
610                 615                 620

Pro Tyr Phe Asp Tyr Trp Gly Gln Gly Thr Leu Val Thr Val Ser Ser
625                 630                 635                 640
```

```
Gly Ser Ser Gly Gly Glu Ile Val Leu Thr Gln Ser Pro Gly Thr Leu
                645                 650                 655

Ser Leu Ser Pro Gly Glu Arg Ala Thr Leu Ser Cys Arg Ala Ser Gln
            660                 665                 670

Ser Val Ser Ser Ser Phe Leu Ala Trp Tyr Gln Gln Lys Pro Gly Gln
        675                 680                 685

Ala Pro Arg Leu Leu Ile Tyr Tyr Ala Ser Ser Arg Ala Thr Gly Ile
    690                 695                 700

Pro Asp Arg Phe Ser Gly Ser Gly Ser Gly Thr Asp Phe Thr Leu Thr
705                 710                 715                 720

Ile Ser Arg Leu Glu Pro Glu Asp Phe Ala Val Tyr Tyr Cys Gln Gln
                725                 730                 735

Thr Gly Arg Ile Pro Pro Thr Phe Gly Gln Gly Thr Lys Val Glu Ile
            740                 745                 750

Lys Ser Ser Ser Ser Gly Ser Ser Ser Gly Ser Ser Ser Ser Ser Gly
        755                 760                 765

Glu Val Gln Leu Leu Glu Ser Gly Gly Gly Leu Val Gln Pro Gly Gly
    770                 775                 780

Ser Leu Arg Leu Ser Cys Ala Ala Ser Gly Phe Thr Phe Ser Ser Phe
785                 790                 795                 800

Ser Met Ser Trp Val Arg Gln Ala Pro Gly Lys Gly Leu Glu Trp Val
                805                 810                 815

Ser Ser Ile Ser Gly Ser Ser Gly Thr Thr Tyr Tyr Ala Asp Ser Val
            820                 825                 830

Lys Gly Arg Phe Thr Ile Ser Arg Asp Asn Ser Lys Asn Thr Leu Tyr
        835                 840                 845

Leu Gln Met Asn Ser Leu Arg Ala Glu Asp Thr Ala Val Tyr Tyr Cys
    850                 855                 860

Ala Lys Pro Phe Pro Tyr Phe Asp Tyr Trp Gly Gln Gly Thr Leu Val
865                 870                 875                 880

Thr Val Ser Ser Gly Ser Ser Gly Gly Glu Ile Val Leu Thr Gln Ser
                885                 890                 895

Pro Gly Thr Leu Ser Leu Ser Pro Gly Glu Arg Ala Thr Leu Ser Cys
            900                 905                 910

Arg Ala Ser Gln Ser Val Ser Ser Ser Phe Leu Ala Trp Tyr Gln Gln
        915                 920                 925

Lys Pro Gly Gln Ala Pro Arg Leu Leu Ile Tyr Tyr Ala Ser Ser Arg
    930                 935                 940

Ala Thr Gly Ile Pro Asp Arg Phe Ser Gly Ser Gly Ser Gly Thr Asp
945                 950                 955                 960

Phe Thr Leu Thr Ile Ser Arg Leu Glu Pro Glu Asp Phe Ala Val Tyr
                965                 970                 975

Tyr Cys Gln Gln Thr Gly Arg Ile Pro Pro Thr Phe Gly Gln Gly Thr
            980                 985                 990

Lys Val Glu Ile Lys
        995

<210> SEQ ID NO 28
<211> LENGTH: 5
<212> TYPE: PRT
<213> ORGANISM: artificial sequence
<220> FEATURE:
<223> OTHER INFORMATION: antibody sequence (CDR)

<400> SEQUENCE: 28
```

```
Ser Phe Ser Met Ser
1               5

<210> SEQ ID NO 29
<211> LENGTH: 17
<212> TYPE: PRT
<213> ORGANISM: artificial sequence
<220> FEATURE:
<223> OTHER INFORMATION: antibody sequence (CDR)

<400> SEQUENCE: 29

Ser Ile Ser Gly Ser Ser Gly Thr Thr Tyr Tyr Ala Asp Ser Val Lys
1               5                   10                  15

Gly

<210> SEQ ID NO 30
<211> LENGTH: 7
<212> TYPE: PRT
<213> ORGANISM: artificial sequence
<220> FEATURE:
<223> OTHER INFORMATION: antibody sequence (CDR)

<400> SEQUENCE: 30

Pro Phe Pro Tyr Phe Asp Tyr
1               5

<210> SEQ ID NO 31
<211> LENGTH: 12
<212> TYPE: PRT
<213> ORGANISM: artificial sequence
<220> FEATURE:
<223> OTHER INFORMATION: antibody sequence (CDR)

<400> SEQUENCE: 31

Arg Ala Ser Gln Ser Val Ser Ser Ser Phe Leu Ala
1               5                   10

<210> SEQ ID NO 32
<211> LENGTH: 7
<212> TYPE: PRT
<213> ORGANISM: artificial sequence
<220> FEATURE:
<223> OTHER INFORMATION: antibody sequence (CDR)

<400> SEQUENCE: 32

Tyr Ala Ser Ser Arg Ala Thr
1               5

<210> SEQ ID NO 33
<211> LENGTH: 9
<212> TYPE: PRT
<213> ORGANISM: artificial sequence
<220> FEATURE:
<223> OTHER INFORMATION: antibody sequence (CDR)

<400> SEQUENCE: 33

Gln Gln Thr Gly Arg Ile Pro Pro Thr
1               5

<210> SEQ ID NO 34
<211> LENGTH: 5
<212> TYPE: PRT
<213> ORGANISM: artificial sequence
<220> FEATURE:
<223> OTHER INFORMATION: GGGGS linker
```

```
<400> SEQUENCE: 34

Gly Gly Gly Gly Ser
1               5

<210> SEQ ID NO 35
<211> LENGTH: 5
<212> TYPE: PRT
<213> ORGANISM: artificial sequence
<220> FEATURE:
<223> OTHER INFORMATION: GGGGA linker

<400> SEQUENCE: 35

Gly Gly Gly Gly Ala
1               5

<210> SEQ ID NO 36
<211> LENGTH: 229
<212> TYPE: PRT
<213> ORGANISM: artificial sequence
<220> FEATURE:
<223> OTHER INFORMATION: L19 Diabody

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Ser Ser Gly Gly Glu Ile Val Leu Thr Gln Ser
        115                 120                 125

Pro Gly Thr Leu Ser Leu Ser Pro Gly Glu Arg Ala Thr Leu Ser Cys
    130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
        195                 200                 205

Tyr Cys Gln Gln Thr Gly Arg Ile Pro Pro Thr Phe Gly Gln Gly Thr
    210                 215                 220

Lys Val Glu Ile Lys
225
```

EDB TARGETING IL-12 COMPOSITIONS

CROSS-REFERENCE OF RELATED APPLICATIONS

This application is a § 371 of International Application No. PCT/EP2019/053136, filed Feb. 8, 2019, which claims the benefit of priority to EP Provisional application Ser. No. 18/156,141.6, filed Feb. 9, 2018; and EP Provisional application Ser. No. 18/179,313.4, filed Jun. 22, 2018; all of which are incorporated by reference in their entirety.

SEQUENCE LISTING

The instant application contains a Sequence Listing with 36 sequences which has been submitted via EFS-Web and is hereby incorporated by reference in its entirety. Said ASCII copy, created on Aug. 3, 2020 is named SEQLIST and is 40,720 bytes in size.

FIELD OF THE INVENTION

The present application relates to compositions comprising a cytokine, an antigen binding domain, and an improved linker.

BACKGROUND

IL-12 is a heterodimeric cytokine comprising two disulfide-linked subunits, p35 and p40. IL-12 stimulates the production of IFNγ from T-cells and natural killer cells, and also induces differentiation of Th1 helper cells. IL-12 is a key mediator of innate and cell-mediated immunity, with the potential for anti-cancer and anti-metastatic activity.

Like many other cytokines, however, the administration of IL-12 is associated with severe toxicity (Car et al., 1999), even at doses as low as 1 μg per kg per day, discouraging its development as an anticancer drug.

SUMMARY OF THE INVENTION

The present invention provides, among other things, improved compositions and methods that can be used to effectively treat various diseases and disorders associated with the expression of EDB fibronectin.

In particular, the present invention provides IL-12 linked EDB binding domains having preferred therapeutic properties over known recombinant IL-12 constructs. The compositions described herein surprisingly are superior to previously known IL-12 constructs designed to target EDB and solve the long-known problem of safely and effectively administering IL-12 for the targeted treatment of a disease or disorder, e.g., a cancer. The compositions and methods described herein provide for improved therapeutic potential of IL-12 by enhancing one or more of its biodistribution profile, its tolerability, its therapeutic window, and its efficacy in reaching the site of disease. The constructs described herein also surprisingly exhibit superior manufacturability.

There remains a need in the art for improvements in tissue penetration of immunocytokine treatments. There is also a need in the art for improved manufacturing of immunocytokine treatments as these are highly complex proteins which are difficult to produce.

It is hence an object of the present invention to provide improved versions immunocytokines, e.g., of protein therapeutics comprising an IL-12 and an EDB fibronectin binding domain. It is a further object of the present invention to provide immunocytokines which exhibit more efficient production. It is another object of the present invention to provide immunocytokines with improved in vivo performance, e.g., target binding or tissue penetration.

The present invention provides compositions comprising an antigen-binding domain and a cytokine having such superior properties. The invention and general advantages of its features, including suitable linkers, will be discussed in detail below.

According to one aspect of the invention, a composition is provided comprising
  a. an IL-12 protein comprising a first IL-12 subunit and a second IL-12 protein subunit;
  b. a peptide or protein comprising an EDB binding domain; and
  c. a linker between the IL-12 protein and the peptide or protein comprising the EDB binding domain.

Preferably, the two subunits of IL-12 are joined to one another by a given linker, according to the following scheme (N→C orientation): p40-linker 1-p35.

Preferably IL-12 is human IL-12. According to some embodiments of the invention, the single chain diabody binds to a splice isoform of fibronectin. Preferably, said extra-domain B (ED-B) of fibronectin is the extra-domain B of human fibronectin (UniProt: P02751).

In some embodiments, the linker between the IL-12 protein and the peptide or protein comprising the EDB binding domain comprises GSADGGSSAGGSDAG (SEQ ID NO: 4).

In some embodiments, the peptide or protein comprising the EDB binding domain comprises an scFv. In some embodiments, the peptide or protein comprising the EDB binding domain is a diabody. In some embodiments, the peptide or protein comprising the EDB binding domain is a single chain diabody.

In some embodiments, the first subunit of the IL-12 protein is a p40 and the second subunit is a p35.

In some embodiments, the first subunit of the IL-12 protein is a p40 comprising an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO:1 or a fragment thereof, wherein the IL-12 protein can activate an IL-12 receptor.

In some embodiments, the second subunit of the IL-12 protein is a p35 comprising an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO:3 or a fragment thereof, wherein the IL-12 protein can activate an IL-12 receptor.

In some embodiments, the peptide or protein comprising an EDB binding domain is monospecific or bispecific.

In some embodiments, the peptide or protein comprising an EDB binding domain binds to the extra-domain B (ED-B) of fibronectin.

In some embodiments, the peptide or protein comprising an EDB binding domain comprises an amino acid sequence having at least 75%, 80%, 85%, 90%, 91%, 92%, 93%, 94%, 95%, 96%, 97%, 98%, 99%, or 100% identity to one or more of the amino acid sequences set forth in SEQ ID NOs: 28 to 33.

In some embodiments, the peptide or protein comprising an EDB binding domain comprises each of the amino acid sequences of SEQ ID NOs: 28 to 33.

In some embodiments, the peptide or protein comprising an EDB binding domain comprises an amino acid sequence having at least 75%, 80%, 85%, 90%, 91%, 92%, 93%, 94%, 95%, 96%, 97%, 98%, 99%, or 100% identity to one or more of the amino acid sequences set forth in SEQ ID NOs: 7 and 5.

In some embodiments, the peptide or protein comprising an EDB binding domain comprises each of the amino acid sequences set forth in SEQ ID NOs: 7 and 5.

In some embodiments, the peptide or protein comprising an EDB binding domain comprises at least one of
  a) the sequence pair according to the above description, with the proviso that at least one of the domains has a sequence identity of ≥80% relative to SEQ ID NO:7 or SEQ ID NO:5, respectively and/or
  b) the sequence pair according to the above description, with the proviso that at least one of the domains has up to 10 amino acid substitutions relative to SEQ ID NO:7 or SEQ ID NO:5, respectively,
while maintaining its capability to bind to the extra-domain B (ED-B) of fibronectin.

In some embodiments, the peptide or protein comprises at least one amino acid substitution where the at least one amino acid substitution is a conservative amino acid substitution.

In some embodiments, the peptide or protein comprising an EDB binding domain
  has a target binding affinity of ≥50% to the extra-domain B (ED-B) of fibronectin, compared to one of the peptides or proteins comprising an anti-EDB binding domain as described above and/or
  competes for binding to the extra-domain B (ED-B) of fibronectin with one of peptides or proteins comprising an EDB binding domain as described above.

In some embodiments, the peptide or protein comprising an EDB binding domain comprises two L19 VH domains and two L19 VL domains.

In some embodiments, the two L19 VH domains have the same amino acid sequence;
  the two L19 VH domains have a different amino acid sequence;
  the two L19 VL domains have the same amino acid sequence; or
  the two L19 VL domains have a different amino acid sequence.

In some embodiments, the peptide or protein comprising an EDB binding domain comprises one L19 VH domain and one L19 VL domain.

In some embodiments, the composition comprises:
  a p40 domain linked to a p35 domain by a first linker (also called "linker 1");
  a first L19 VH domain linked to the p35 domain by a SAD linker;
  a first L19 VL domain linked to the first L19 VH domain by a third linker (also called "linker 3");
  a second L19 VH domain linked to the first L19 VL domain by a fourth linker (also called "linker 4");
  a second L19 VL domain linked to the second L19 VH domain by a fifth linker (also called "linker 5").

In some embodiments, the third linker and fifth linker comprise the same amino acid sequence, and/or can be replaced against one another.

In some embodiments, the p40 domain comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 1 or a fragment thereof.

In some embodiments, the p35 domain comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 3 or a fragment thereof.

In some embodiments, the first linker ("linker 1") is a GS linker.

In some embodiments, the first linker comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 2.

In some embodiments, the first L19 VH domain, the second L19 VH domain, or both comprise an amino acid sequence having at least 75%, 80%, 85%, 90%, 91%, 92%, 93%, 94%, 95%, 96%, 97%, 98%, 99%, or 100% identity to at least one amino acid sequence set forth in SEQ ID NOs: 28-30.

In some embodiments, the first L19 VL domain, the second L19 VL domain, or both comprise an amino acid sequence having at least 75%, 80%, 85%, 90%, 91%, 92%, 93%, 94%, 95%, 96%, 97%, 98%, 99%, or 100% identity to at least one amino acid sequence set forth in SEQ ID NOs: 31-33.

In some embodiments, the first L19 VH domain, the second L19 VH domain, or both comprise an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 7.

In some embodiments, the first L19 VL domain, the second L19 VL domain, or both comprise an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 5.

In some embodiments, the SAD linker comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 4.

In some embodiments, the third linker ("linker 3") is a GS linker.

In some embodiments, the third linker comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 6.

In some embodiments, the fifth linker ("linker 5") is a GS linker.

In some embodiments, the fifth linker comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 6.

In some embodiments, the third linker ("linker 3") and fifth linker ("linker 5") comprise the same amino acid sequence, and/or can be replaced against one another.

In some embodiments, the fourth linker ("linker 4") is a GS linker.

In some embodiments, the fourth linker comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 8.

In some embodiments, the composition comprises an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 16.

In some embodiments, the composition consists of an amino acid sequence having at least 75%, 80%, 85%, 90%, 91%, 92%, 93%, 94%, 95%, 96%, 97%, 98%, 99%, or 100% identity to the amino acid sequence set forth in SEQ ID NO: 16.

According to another aspect of the invention, the use of the composition according to any one of the aforementioned claims (for the manufacture of a medicament) is provided in the treatment of a human or animal subject being diagnosed for,
suffering from or
being at risk of developing a neoplastic disease, or for the prevention of such condition.

In some embodiments, the neoplastic disease is selected from the group consisting of malignant melanoma, non-small cell lung cancer (NSCLC), renal cell carcinoma, urothelial carcinoma, head and neck squamous cell carcinoma (HNSCC), microsatellite instability-high (MSI-H) or mismatch repair deficient (dMMR) metastatic colorectal cancer, hepatocellular cancer, gastric cancer, squamous cell carcinoma of the skin, cervical cancer, and diffuse large B-cell lymphoma (DLBCL).

According to another aspect of the invention, the use of the composition according to the above disclosure (for the manufacture of a medicament) for the inhibition of angiogenesis in a human or animal subject is provided.

According to another aspect of the invention, a pharmaceutical composition comprising at least the composition according to the above description, and optionally one or more pharmaceutically acceptable excipients, is provided.

According to another aspect of the invention, a combination comprising (i) the composition according to the above description or the pharmaceutical composition according to the above description and (ii) one or more therapeutically active compounds is provided.

According to another aspect of the invention, a method for treating or preventing a disorder or condition associated with expression or overexpression of ED-B fibronectin, comprising administering to a subject in need thereof an effective amount of the composition according to the above description, the pharmaceutical composition according to the above description, or the combination according to the above description is provided.

According to another aspect of the invention, a therapeutic kit of parts is provided, comprising:

a) the composition according to the above description, the pharmaceutical composition according to the above description, or the combination according to the above description,
b) an apparatus for administering the composition, composition or combination, and
c) instructions for use.

BRIEF DESCRIPTION OF THE DRAWINGS

FIGS. 1A-1B: Results of protein expression experiments. See below for materials and methods.

FIG. 1A: A 15-mer linker having the amino acid sequence of SEQ ID NO:4 (nicknamed "SAD" herein) shows by far the best production yields of all variants (also called "clones" herein). The yield is almost 100% better than the $2^{nd}$ best variant, DDS.

The two sequences in the line AKKAS are SEQ ID NOs: 9 and 18, the two sequences in the line AP7 are SEQ ID NOs:15 and 19, the two sequences in the line DDS are SEQ ID NOs: 10 and 20, the two sequences in the line AP6 are SEQ ID NOs: 14 and 21, the two sequences in the line G4S are SEQ ID NOs: 11 and 22, the two sequences in the line SES are SEQ ID NOs: 12 and 23, the two sequences in the line alpha3 are SEQ ID NOs: 13 and 24, and the two sequences in the line SAD are SEQ ID NOs: 4 and 25.

Figure 1B:
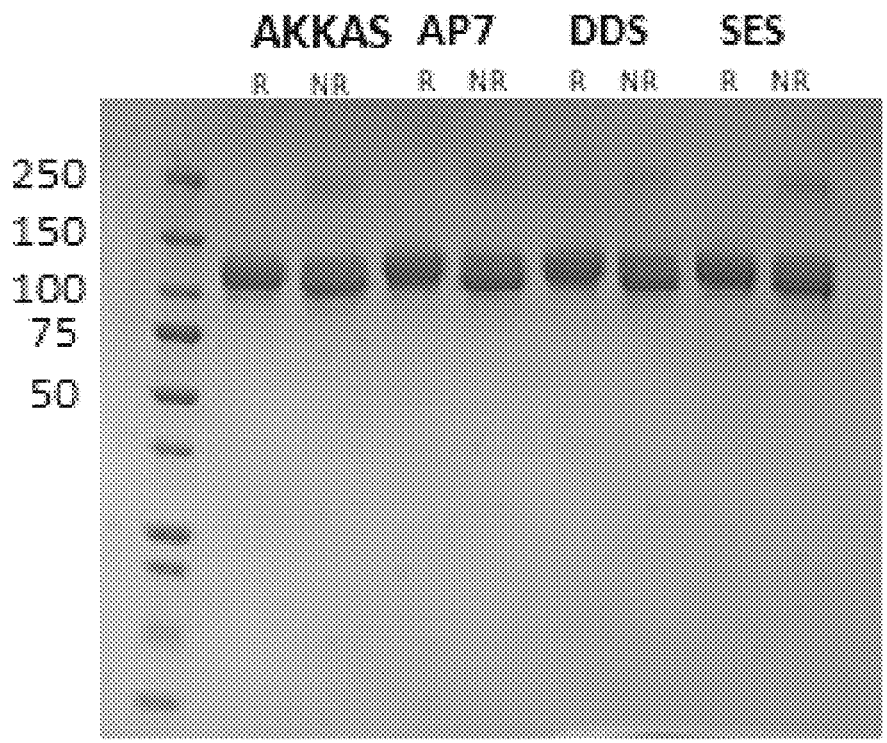
Figure 1B:
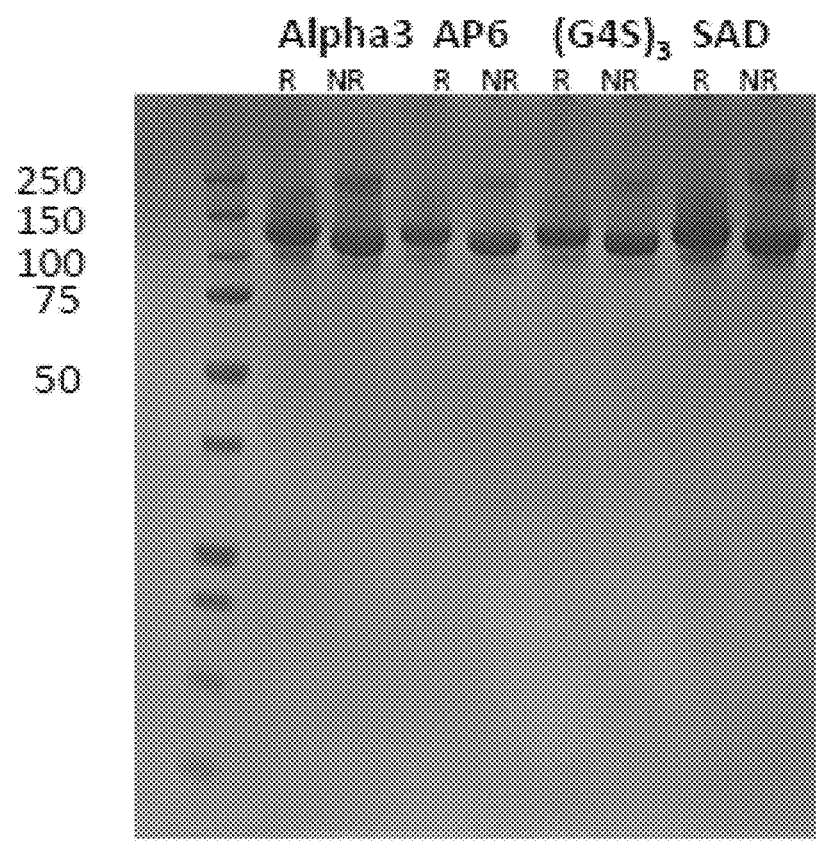

There are N-terminal and C-terminal residues (or 5'- or 3'-nucleotides) in FIG. 1 which are shown in grey. These do not belong to the disclosure of the present application for which a search is necessary. They simply show the framework in which the respective linkers can be embedded.

FIG. 1B: SDS-PAGE characterization displayed a molecular weight around 120 kDa for all variants.

Figure 2:
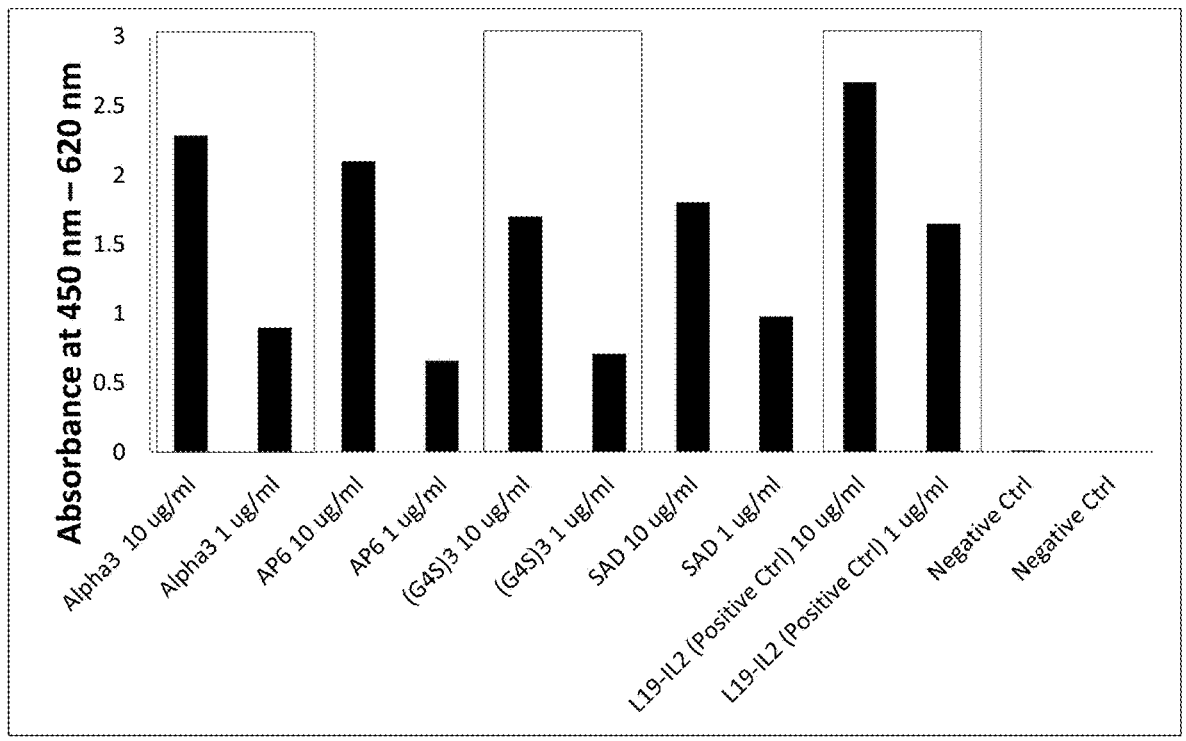
Figure 2:
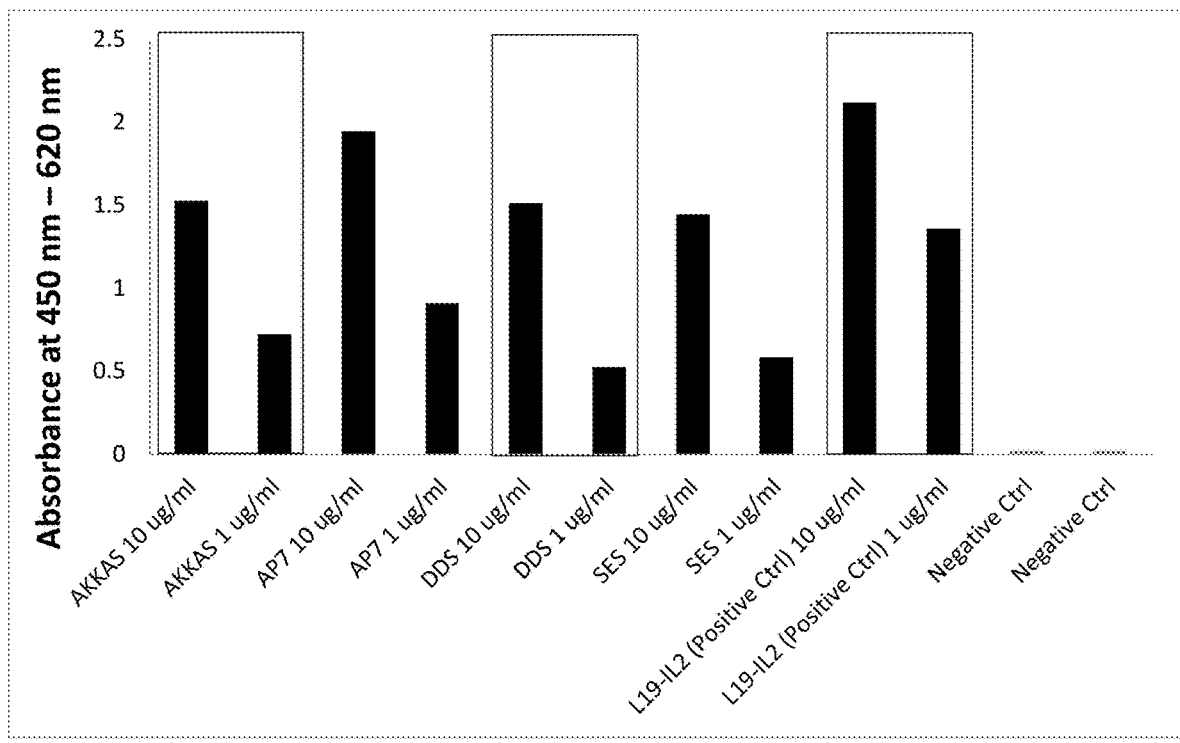

FIG. 2: ELISA experiments. All variants bind to the domain 7B89 of human fibronectin, both at 10 µg/ml and 1 µg/ml concentration.

Figure 3A:
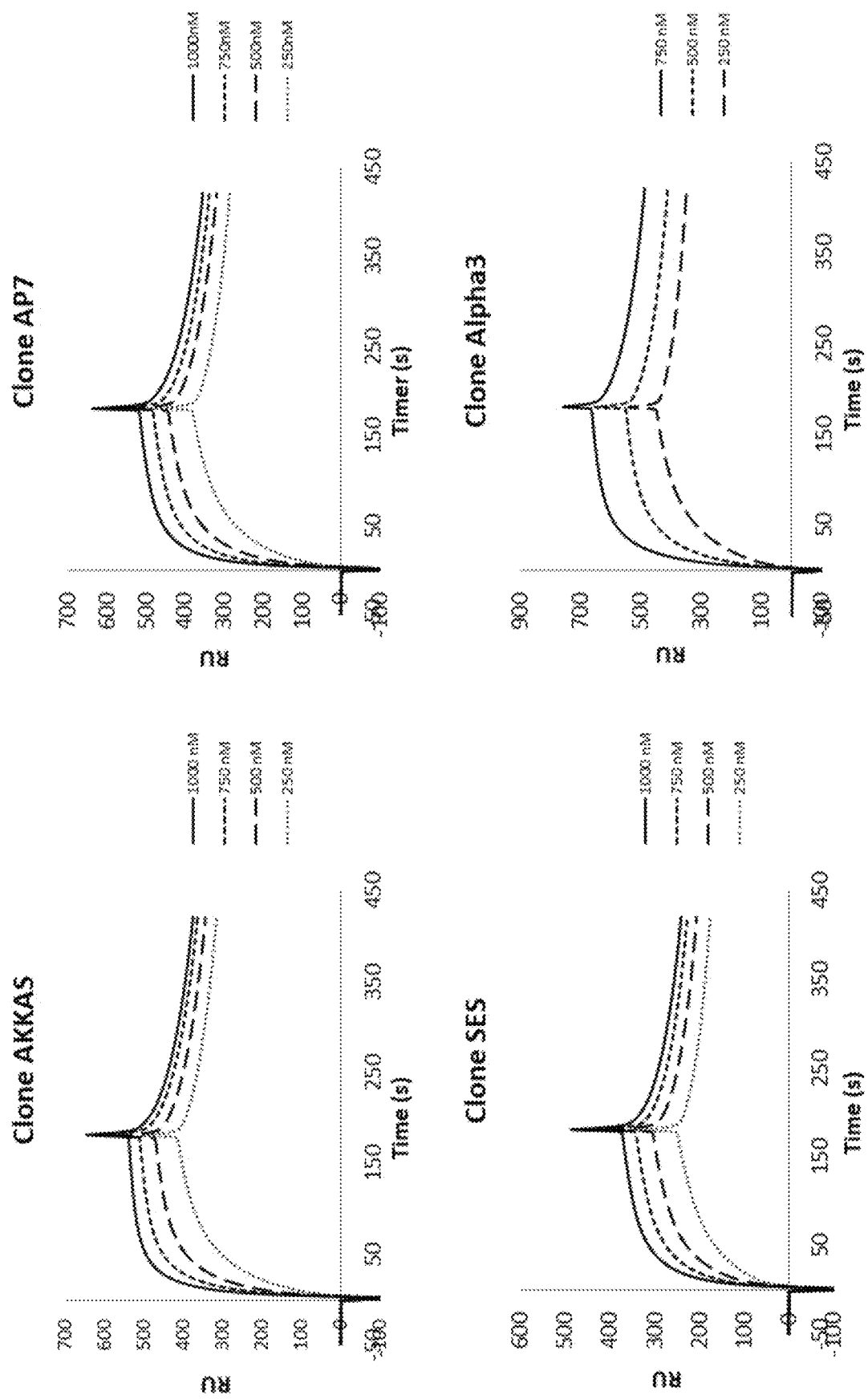
Figure 3B:
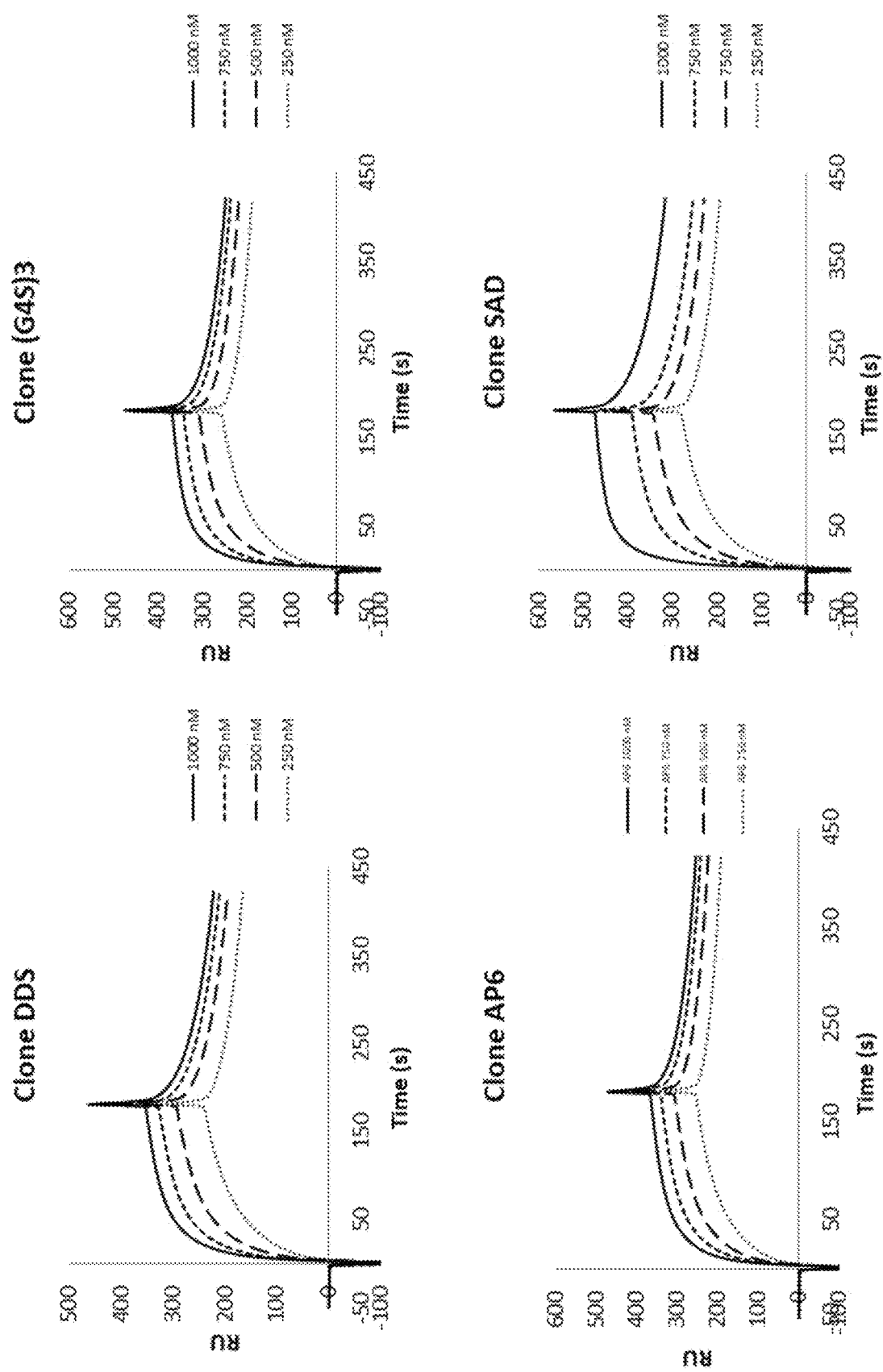

FIG. 3A-3B: Biacore experiments. All variants show similar binding behavior to the domain 7B89 of human fibronectin. FIG. 3A: Biacore experiment of Clone AKKAS, Clone AP7, Clone SES, and Clone Alpha3. FIG. 3B: Biacore experiment of Clone DDS. Clone (G4S)3, Clone AP6, and Clone SAD.

Figure 4A:
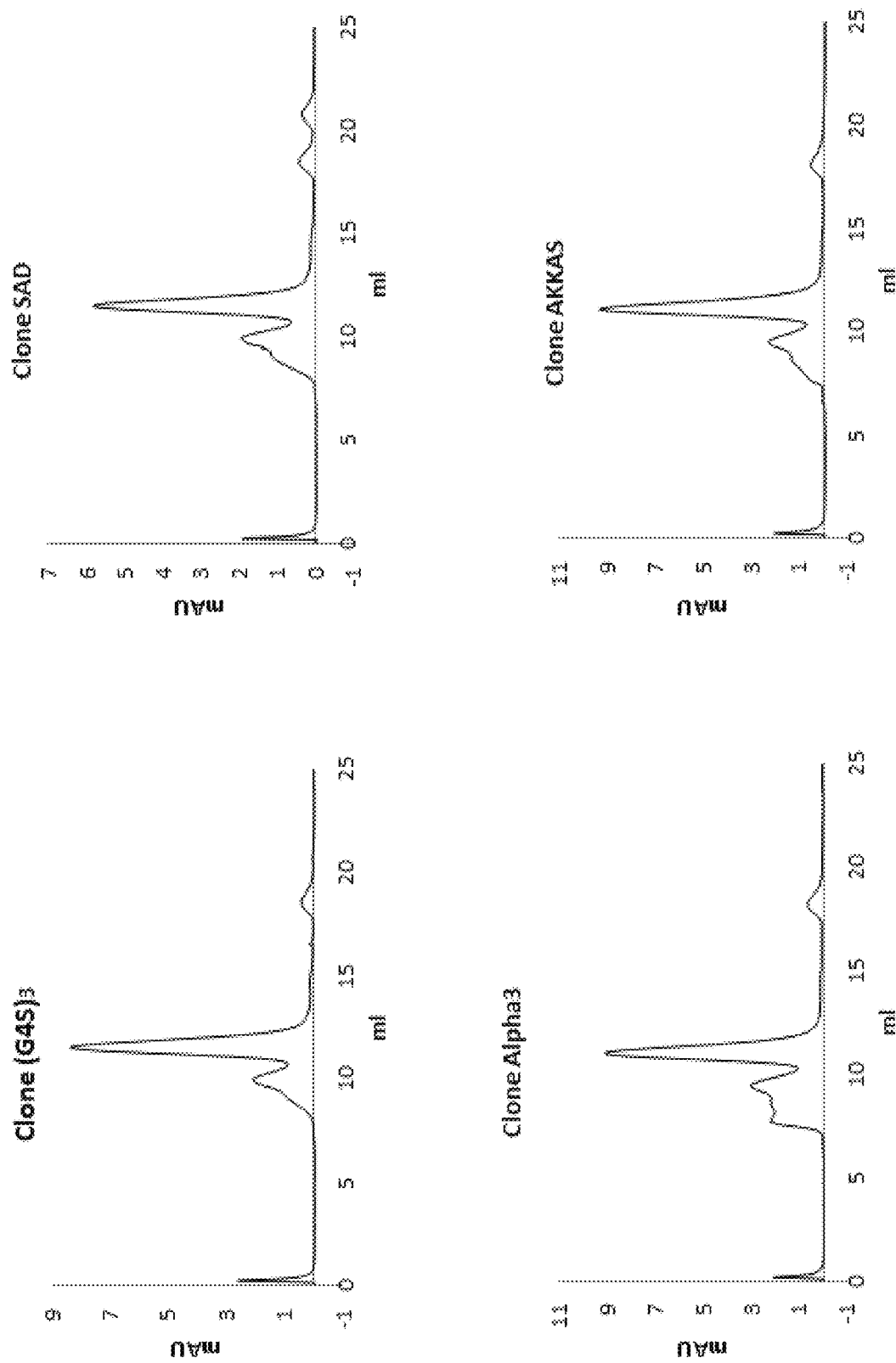
Figure 4B:
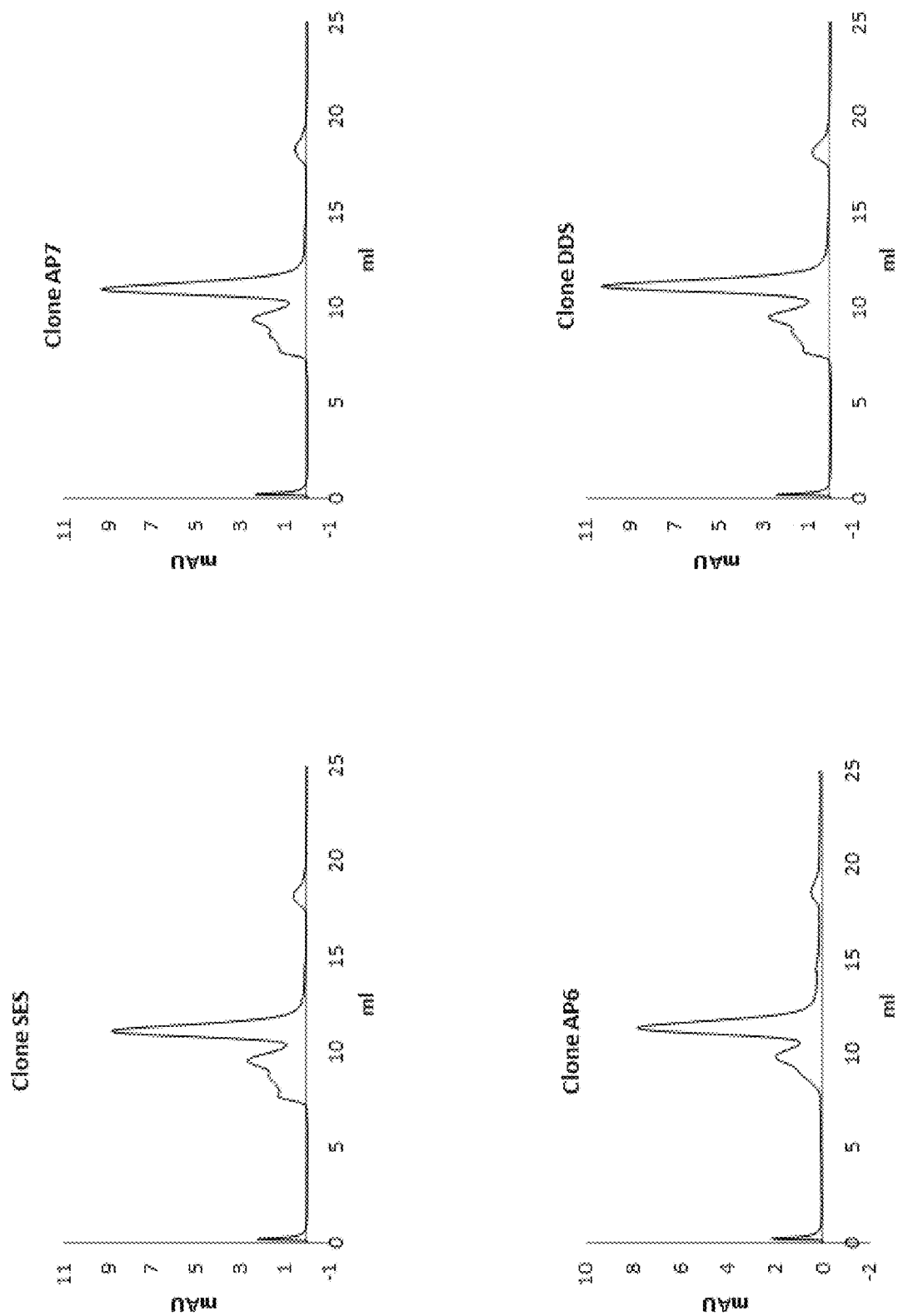

FIG. 4A-4B: Size exclusion chromatography (SEC). All variants showed a comparable aggregation profile with the major peak at 13 ml corresponding to the monomeric immunocytokine, and the smaller peak at 10 ml corresponding to aggregates. FIG. 4A: SEC of Clone (G4S)3, Clone SAD, Clone Alpha3, and Clone AKKAS. FIG. 4B: SEC of Clone SES, Clone AP7, Clone AP6, and Clone DDS.

Figure 5A:
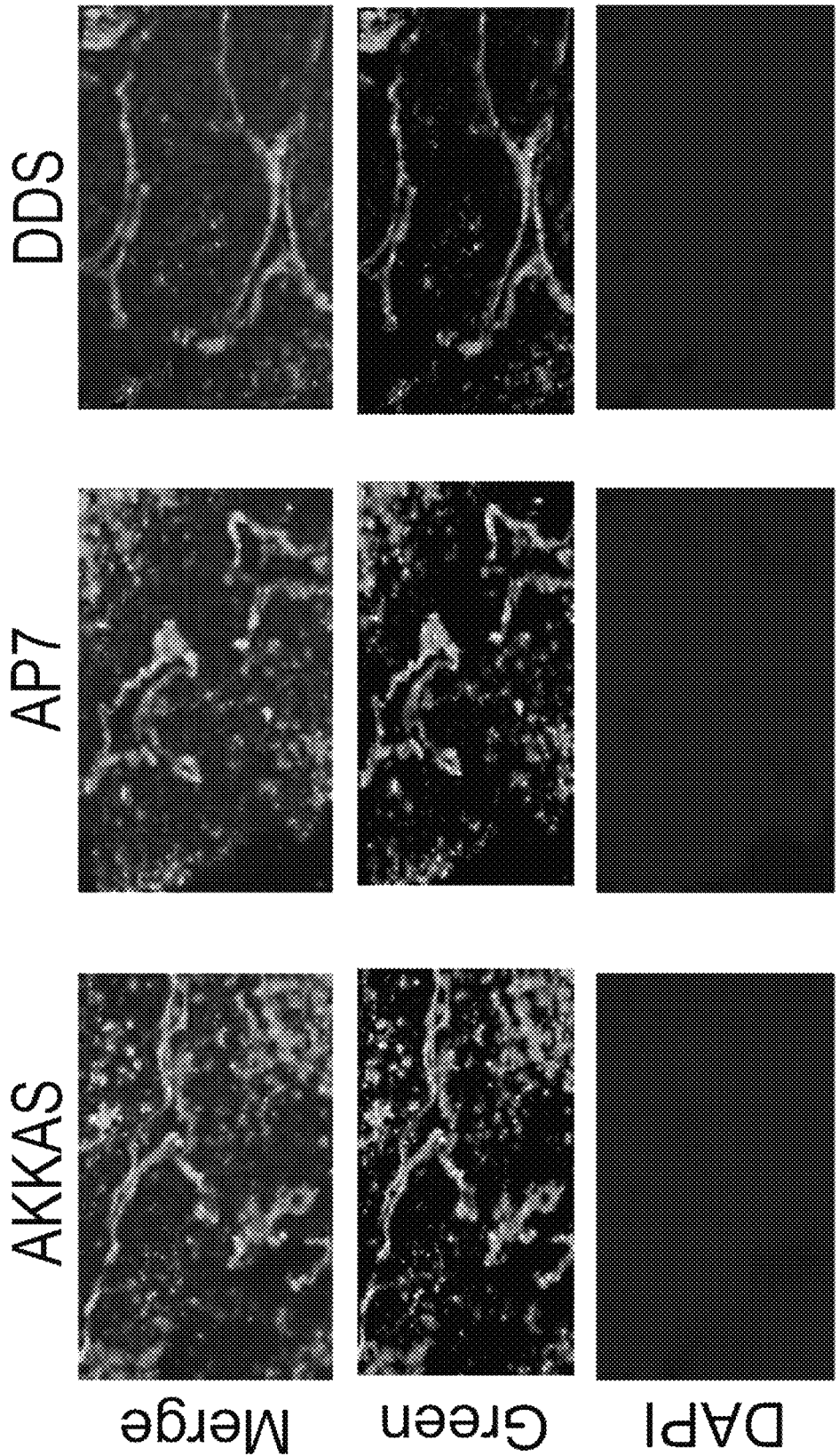
Figure 5B:
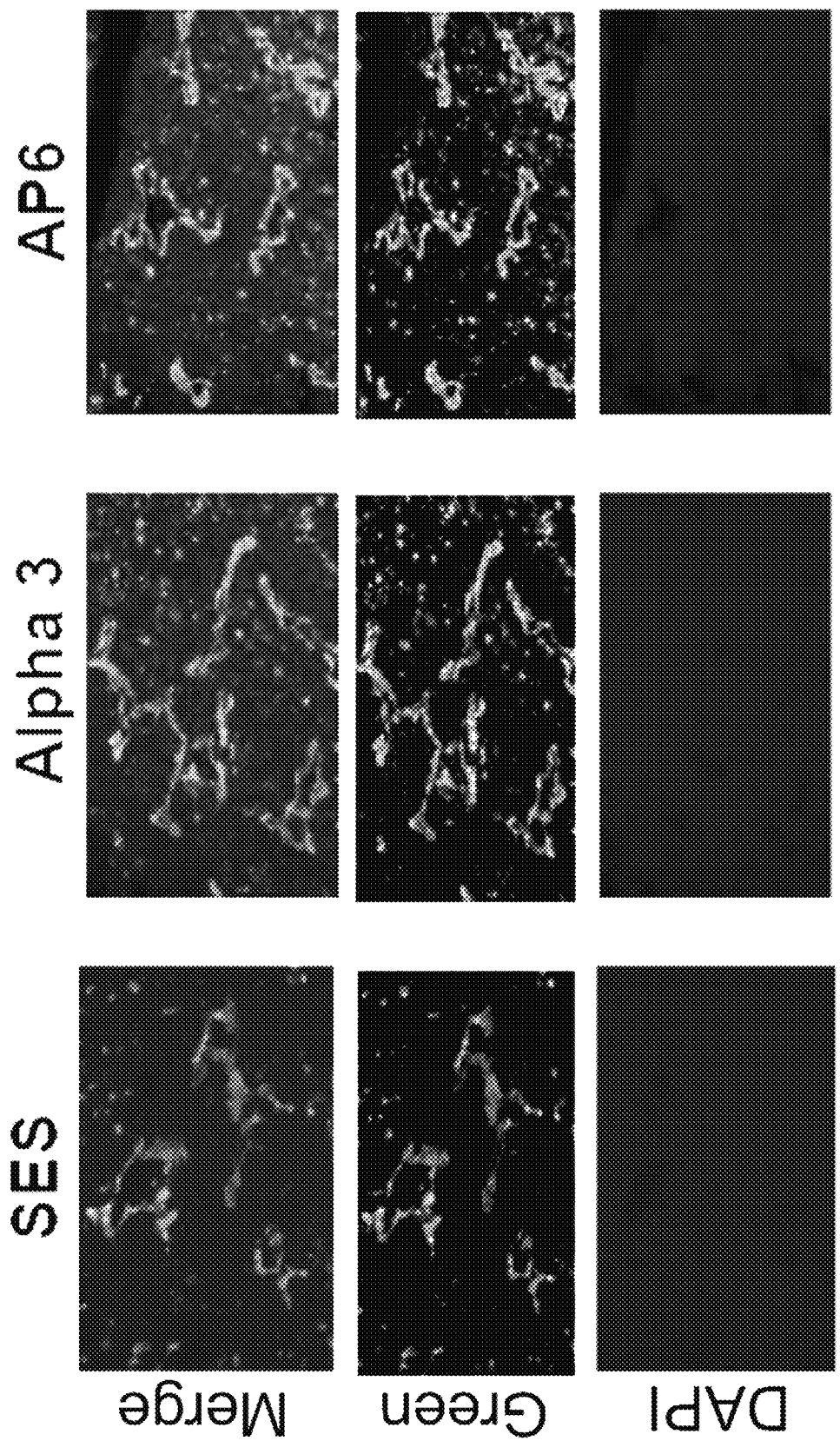
Figure 5C:
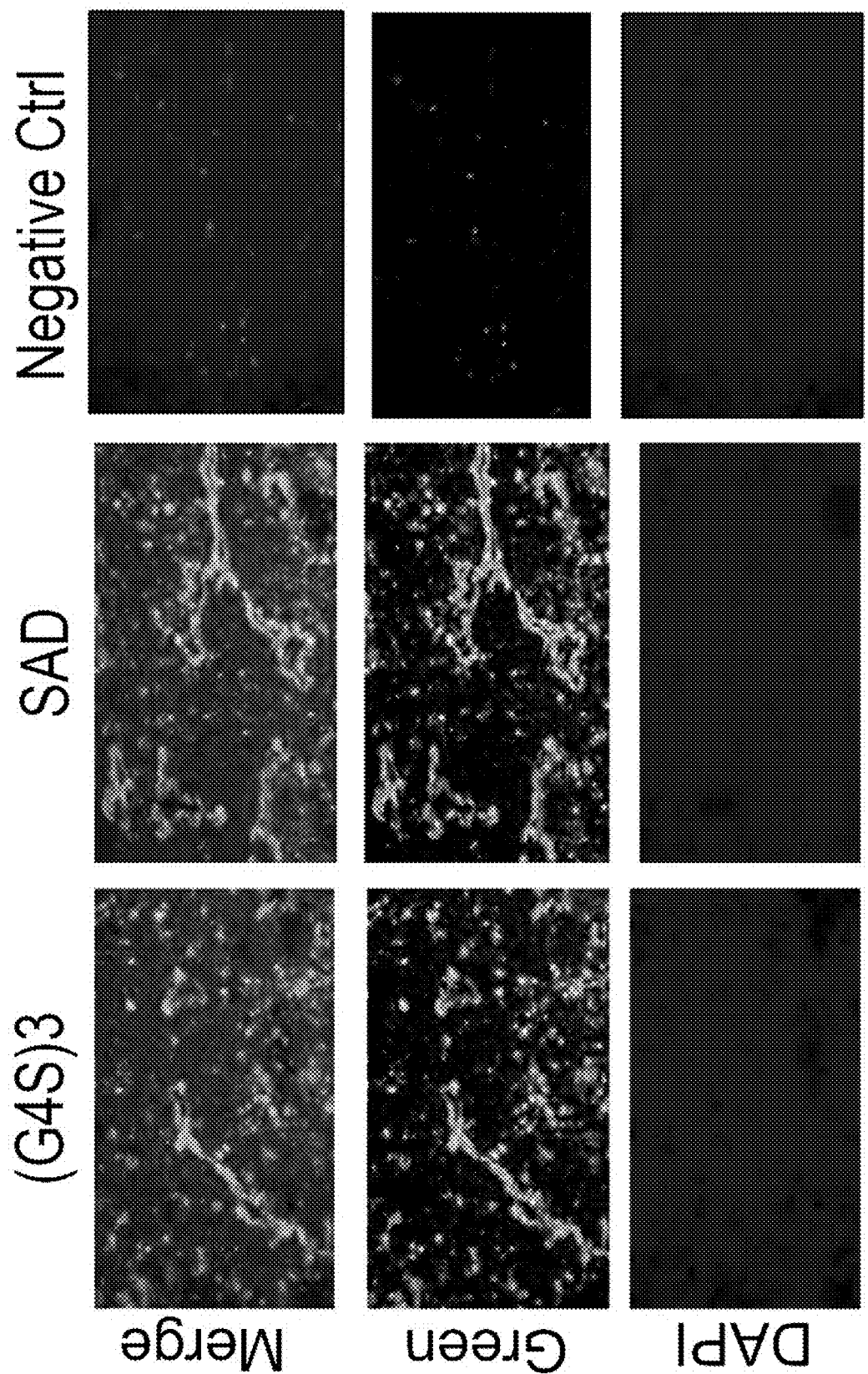

FIG. 5A-5C: Immunofluorescence staining experiments. All variants specifically stained the vasculature of frozen syngeneic F9 teratocarcinoma specimens as compared to the negative control. FIG. 5A: Staining of AKKAS, AP7, and DDS. FIG. 5B: Staining of SES, Alpha 3, and AP. FIG. 5C: Staining of (G4S)3, SAD, and Negative control.

Figure 6A:
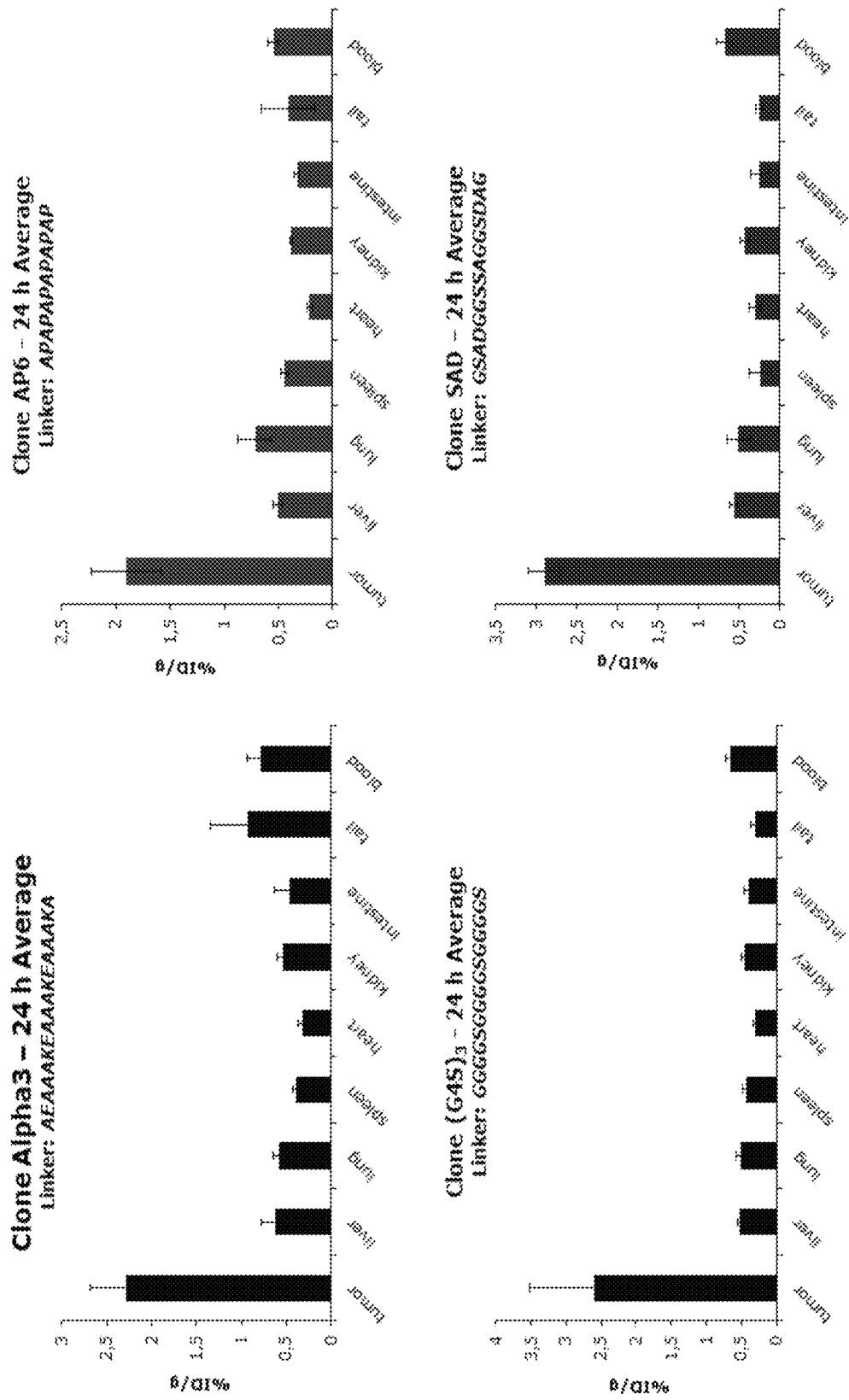
Figure 6B:
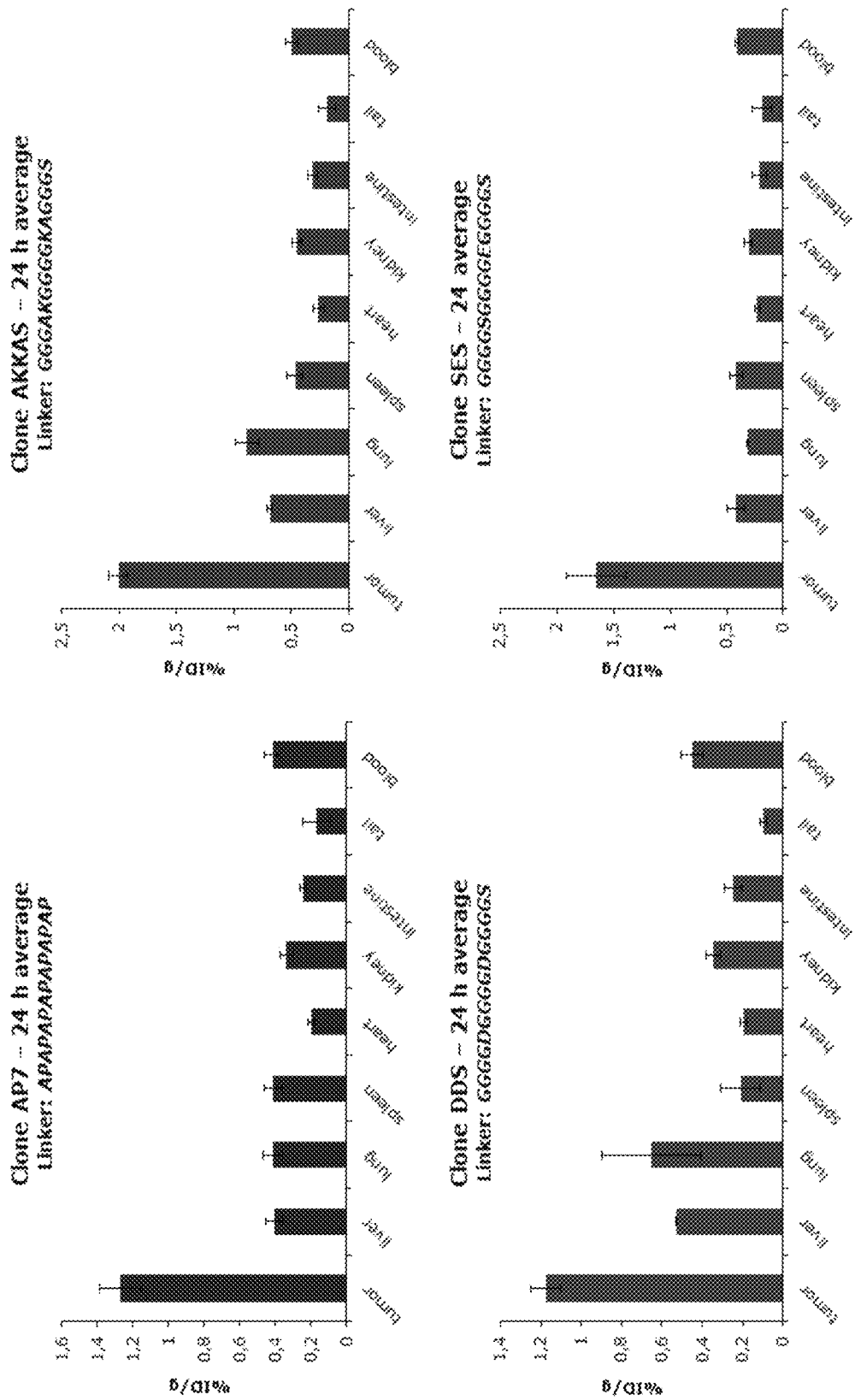
Figure 6C:
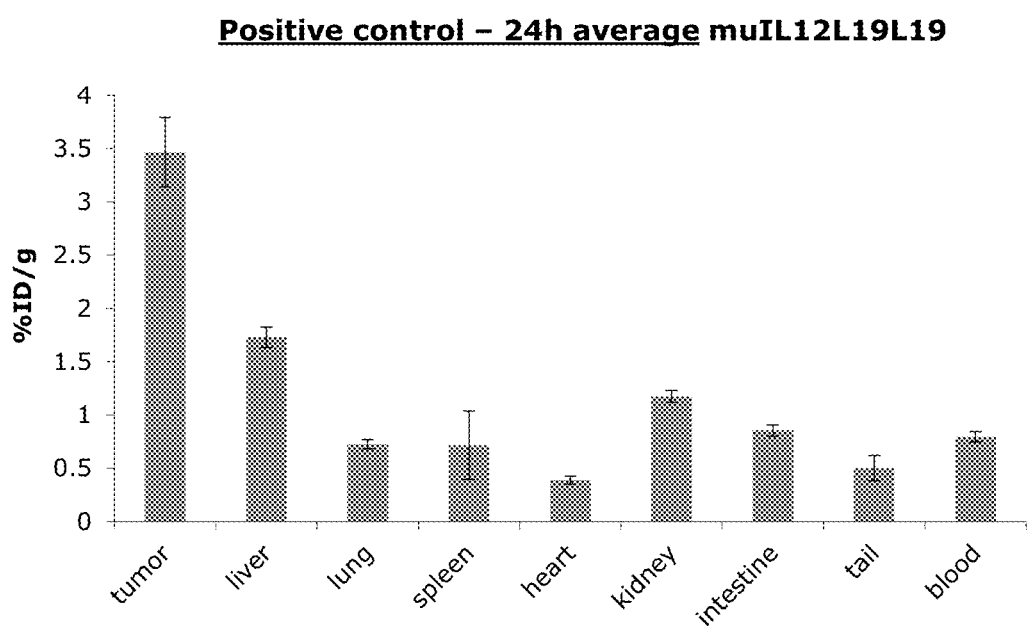

FIG. 6A-6C: In vivo tumor targeting. All variants and a positive control were radioiodinated with 125I and injected (4-9 µg protein/animal) into immunocompetent mice bearing s.c. implanted F9 murine teratocarcinoma. The radioactivity counted 24 hours after the injection showed an accumulation in the tumor for all variants. However, the "SAD" variant showed a superior accumulation in the tumor as compared to the other seven clones (~2.9% ID/g (=injected dose per gram of tissue) vs. the second best, which is (G4S)3, and shows ~2.4% ID/g). FIG. 6A: Radioactivity of Clone Alpha3, Clone AP6, Clone (G4S)3, and Clone SAD. FIG. 6B: Radioactivity of Clone 4P7, Clone AKKAS, Clone DDS, and Clone SES. FIG. 6C: Radioactivity of positive control.

FIGS. 7A-7C and 8A-8C: Exemplary immunocytokine formats using IL-12 and an anti-fibronectin antibody.

FIG. 9A-9D: SEC analysis of the different fusion proteins (FIG. 9A) huIL-12L19L19 "SAD" Batch-A (FIG. 9B) huIL-12L19L19 "SAD" Batch-B (FIG. 9C) huIL-12L19L19 "Old" Batch A (FIG. 9D) huIL-12L19L19 "Old" Batch B.

Figure 10:
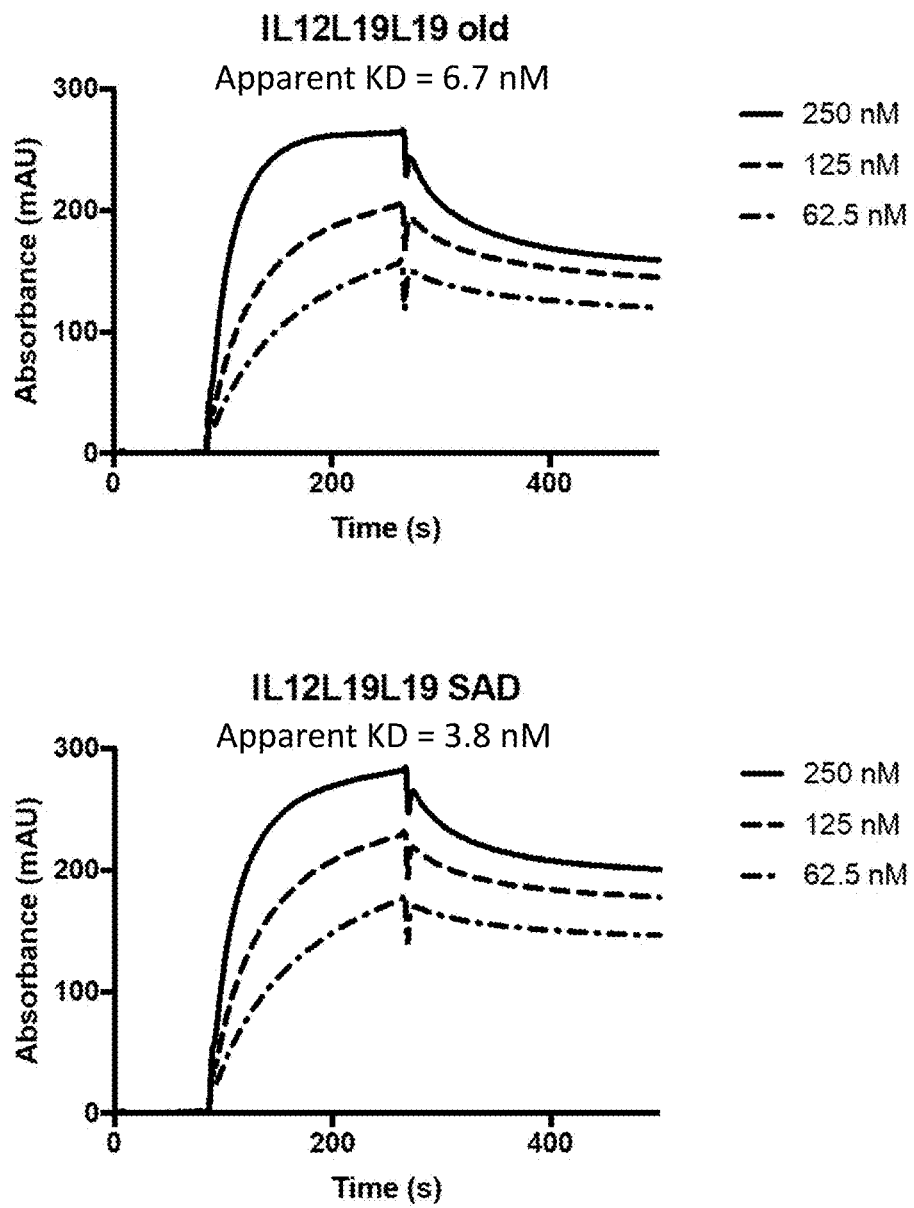

FIG. 10: Biacore experiment. The "SAD" variant showed to have an improved apparent affinity as compared to variant with the "Old" linker toward the fibronectin 7B89 domain (3.8 nM vs 6.7 nM). This surprising result is unexpected, since the variation of the linker may affect the stability of the protein but usually not the affinity to its target.

Figure 11:
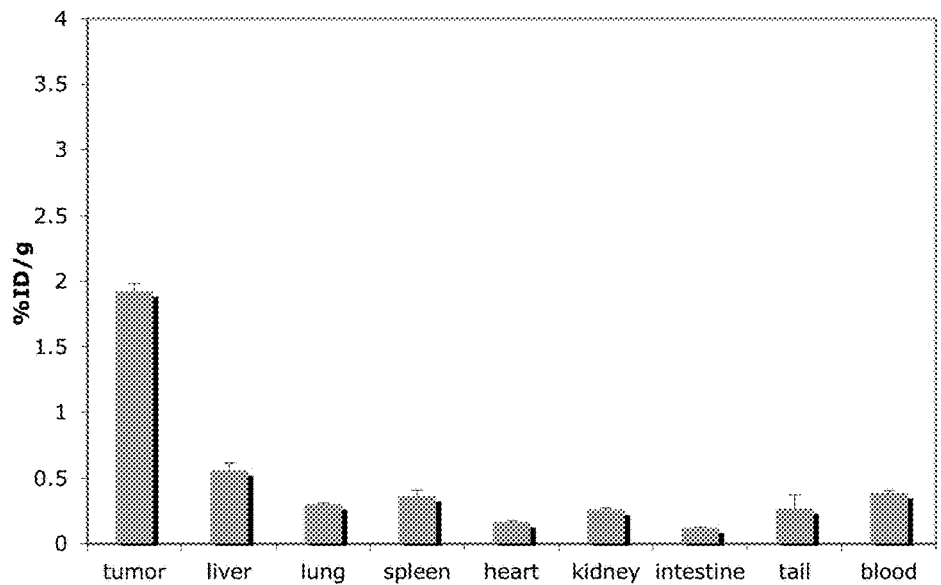
Figure 11:
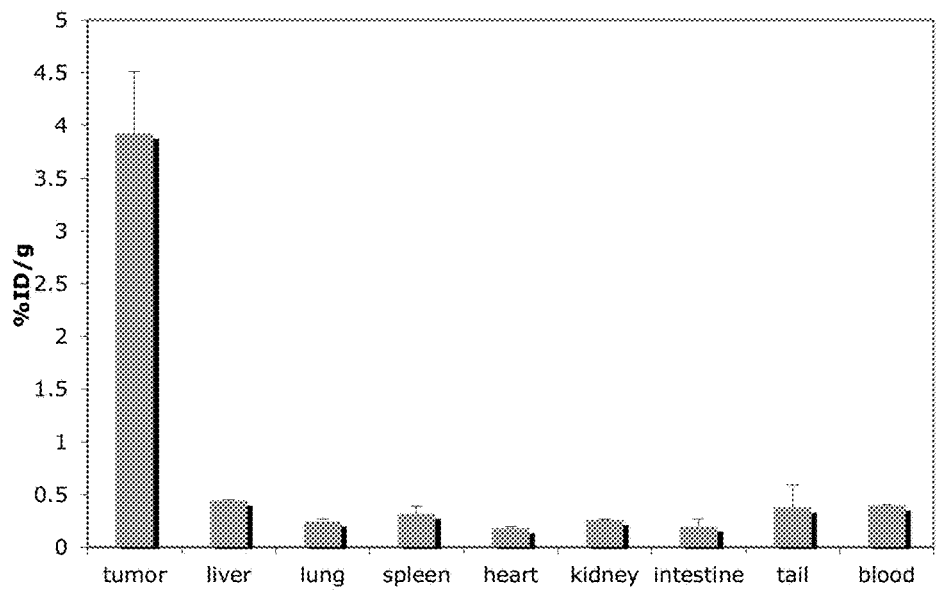

FIG. 11: In vivo tumor targeting experiment. The "SAD" and the "Old" variants were radioiodinated with $^{125}$I and injected (10-11 µg protein/animal) into immunocompetent mice bearing s.c. implanted F9 murine teratocarcinoma. The "SAD" variant showed to have an improved tumor targeting ability as compared to the "Old" linker variant.

DETAILED DESCRIPTION

Definitions

An "antibody" refers to a molecule of the immunoglobulin family comprising a tetrameric structural unit. Each tetramer is composed of two identical pairs of polypeptide chains, each pair having one "light" chain (about 25 kD) and one "heavy" chain (about 50-70 kD), connected through a disulfide bond. Recognized immunoglobulin genes include the κ, λ, α, γ, δ, ε, and µ constant region genes, as well as the myriad immunoglobulin variable region genes. Light chains are classified as either κ or λ. Heavy chains are classified as γ, µ, α, δ, or ε, which in turn define the immunoglobulin classes, IgG, IgM, IgA, IgD, and IgE, respectively. Antibodies can be of any isotype/class (e.g., IgG, IgM, IgA, IgD, and IgE), or any subclass (e.g., IgG1, IgG2, IgG3, IgG4, IgA1, IgA2).

Both the light and heavy chains are divided into regions of structural and functional homology. The terms "constant" and "variable" are used structurally and functionally. The N-terminus of each chain defines a variable (V) region or domain of about 100 to 110 or more amino acids primarily responsible for antigen recognition. The terms variable light chain ($V_L$) and variable heavy chain ($V_H$) refer to these regions of light and heavy chains respectively. The pairing of a $V_H$ and $V_L$ together forms a single antigen-binding site. In addition to V regions, both heavy chains and light chains contain a constant (C) region or domain. A secreted form of an immunoglobulin C region is made up of three C domains, CH1, CH2, CH3, optionally CH4 (Cµ), and a hinge region. A membrane-bound form of an immunoglobulin C region also has membrane and intracellular domains. Each light chain has a $V_L$ at the N-terminus followed by a constant domain (C) at its other end. The constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively. The VL is aligned with the VH and the CL is aligned with the first constant domain of the heavy chain. As used herein, an "antibody" encompasses conventional antibody structures and variations of antibodies. Thus, within the scope of this concept are full length antibodies, chimeric antibodies, humanized antibodies, human antibodies, and antibody fragments thereof.

Antibodies exist as intact immunoglobulin chains or as a number of well-characterized antibody fragments produced by digestion with various peptidases. The term "antibody fragment," as used herein, refers to one or more portions of an antibody that retain the ability to specifically interact with (e.g., by binding, steric hindrance, stabilizing/destabilizing, spatial distribution) an epitope of an antigen. Thus, for example, pepsin digests an antibody below the disulfide linkages in the hinge region to produce F(ab)'2, a dimer of Fab' which itself is a light chain joined to $V_H$-$C_H$1 by a disulfide bond. The F(ab)'2 may be reduced under mild conditions to break the disulfide linkage in the hinge region, thereby converting the F(ab)'2 dimer into a Fab' monomer. The Fab' monomer is essentially Fab with part of the hinge region. Paul, Fundamental Immunology 3d ed. (1993). While various antibody fragments are defined in terms of the digestion of an intact antibody, one of skill will appreciate that such fragments may be synthesized de novo either chemically or by using recombinant DNA methodology. As used herein, an "antibody fragment" refers to one or more portions of an antibody, either produced by the modification of whole antibodies, or those synthesized de novo using recombinant DNA methodologies, that retain binding specificity and functional activity. Examples of antibody fragments include Fv fragments, single chain antibodies (ScFv), Fab, Fab', Fd (Vh and CH1 domains), dAb (Vh and an isolated CDR); diabodies and single chain diabodies; and multimeric versions of these fragments (e.g., F(ab')$_2$) with the same binding specificity. Antibody fragments can also be incorporated into cytokine engrafted proteins to achieve the binding specificity and activity provided in the present disclosure.

A "Fab" domain as used herein comprises a heavy chain variable domain, a constant region CH1 domain, a light chain variable domain, and a light chain constant region CL domain. The interaction of the domains is stabilized by a disulfide bond between the CH1 and CL domains. In some embodiments, the heavy chain domains of the Fab are in the order, from N-terminus to C-terminus, VH-CH and the light chain domains of a Fab are in the order, from N-terminus to C-terminus, VL-CL. In some embodiments, the heavy chain domains of the Fab are in the order, from N-terminus to C-terminus, CH-VH and the light chain domains of the Fab are in the order CL-VL. Although Fabs were historically identified by papain digestion of an intact immunoglobulin, in the context of this disclosure, a "Fab" is typically produced recombinantly by any method. Each Fab fragment is monovalent with respect to antigen binding, i.e., it has a single antigen-binding site.

"Complementarity-determining domains" or "complementarity-determining regions" ("CDRs") interchangeably refer to the hypervariable regions of $V_L$ and $V_H$. CDRs are the target protein-binding site of antibody chains that harbors specificity for such target protein. There are three CDRs (CDR1-3, numbered sequentially from the N-terminus) in each human $V_L$ or $V_H$, constituting about 15-20% of the variable domains. CDRs are structurally complementary to the epitope of the target protein and are thus directly responsible for the binding specificity. The remaining stretches of the $V_L$ or $V_H$, the so-called framework regions (FR), exhibit less variation in amino acid sequence (Kuby, Immunology, 4th ed., Chapter 4. W.H. Freeman & Co., New York, 2000).

Positions of CDRs and framework regions can be determined using various well known definitions in the art, e.g., Kabat, Chothia, international ImMunoGeneTics database (IMGT) and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, CDR amino acid residues in the $V_H$ are numbered 31-35 (HCDR1), 50-65 (HCDR2), and 95-102 (HCDR3); and the CDR amino acid residues in the $V_L$ are numbered 24-34 (LCDR1), 50-56 (LCDR2), and 89-97 (LCDR3). Under Chothia, CDR amino acids in the $V_H$ are numbered 26-32 (HCDR1), 52-56 (HCDR2), and 95-102 (HCDR3); and the amino acid residues in $V_L$ are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions (FR). The term "variable region" or "V-region" interchangeably refer to a heavy or light chain comprising FR1-CDR1-FR2-CDR2-FR3-CDR3-FR4. A V-region can be naturally occurring, recombinant or synthetic. In this application, antibody light chains and/or antibody heavy chains may, from time to time, be collectively referred to as "antibody chains." As provided and further described herein, an "antibody variable light chain" or an "antibody variable heavy chain" and/or a "variable region" and/or an "antibody chain" optionally comprises a cytokine polypeptide sequence engrafted into a CDR.

The C-terminal portion of an immunoglobulin heavy chain as disclosed herein, comprising, e.g., CH2 and CH3 domains, is the "Fc" domain. An "Fc region" as used herein refers to the constant region of an antibody excluding the first constant region (CH1) immunoglobulin domain. Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). "Fc region" may refer to this region in isolation or this region in the context of an antibody or antibody fragment. "Fc region" includes naturally occurring allelic variants of the Fc region, e.g., in the CH2 and CH3 region, including, e.g., modifications that modulate effector function. Fc regions also include variants that don't result in alterations to biological function. For example, one or more amino acids are deleted from the N-terminus or C-terminus of the Fc region of an immunoglobulin without substantial loss of biological function. For example, in certain embodiments a C-terminal lysine is modified replaced or removed. In particular embodiments one or more C-terminal residues in the Fc region is altered or removed. In certain embodiments one or more C-terminal residues in the Fc (e.g., a terminal lysine) is deleted. In certain other embodiments one or more C-terminal residues in the Fc is substituted with an alternate amino acid (e.g., a terminal lysine is replaced). Such variants are selected according to general rules known in the art so as to have minimal effect on activity (see, e.g., Bowie, et al., Science 247:306-1310, 1990). The Fc domain is the portion of the immunoglobulin (Ig) recognized by cell receptors, such as the FcR, and to which the complement-activating protein, Cl q, binds. The lower hinge region, which is encoded in the 5' portion of the CH2 exon, provides flexibility within the antibody for binding to FcR receptors.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

A "humanized" antibody is an antibody that retains the reactivity (e.g., binding specificity, activity) of a non-human antibody while being less immunogenic in humans. This can be achieved, for instance, by retaining non-human CDR regions and replacing remaining parts of an antibody with human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

A "human antibody" includes antibodies having variable regions in which both the framework and CDR regions are derived from sequences of human origin. Furthermore, if an antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Human antibodies may include amino acid residues not encoded by human sequences (e.g., mutations introduced by random or site-specific mutagenesis in vitro or by somatic mutation in vivo, or a conservative substitution to promote stability or manufacturing).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. As used herein, the term "peptide or protein comprising an EDB binding domain" relates to a peptide or protein which, as a whole or by virtue of a portion/fragment thereof, binds to EDB, i.e., Extra domain-B containing fibronectin.

Generally, a peptide can for example be a monomeric molecule having a length of ≥3 amino acid residues and ≤50 amino acid residues (hence, an oligo- or polypeptide), while a protein can for example be a monomeric or bi- or polymeric molecule with one or more protein each chain having a length of ≥50 amino acid residues.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alter, add or delete a single amino acid or a small percentage of amino acids in the encoded sequence are a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In this context, a "conservative amino acid substitution", as used herein, has a smaller effect on antibody function than a non-conservative substitution. Although there are many ways to classify amino acids, they are often sorted into six main groups on the basis of their structure and the general chemical characteristics of their R groups.

In some embodiments, a "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Other conserved amino acid substitutions can also occur across amino acid side chain families, such as when substituting an asparagine for aspartic acid in order to modify the charge of a peptide. Conservative changes can further include substitution of chemically homologous non-natural amino acids (i.e. a synthetic non-natural hydrophobic amino acid in place of leucine, a synthetic non-natural aromatic amino acid in place of tryptophan).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The disclosure provides polypeptides or polynucleotides that are substantially identical to the polypeptides or polynucleotides, respectively, exemplified herein. Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

As used herein, the terms "treat," "treating," or "treatment" of any disease or disorder refer in some embodiments, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" or "prophylaxis" refers to preventing or delaying the onset or development or progression of a disease or disorder.

The term "co-administer" refers to the simultaneous presence of two (or more) active agents in an individual. Active agents that are co-administered can be concurrently or sequentially delivered.

Various aspects of the invention are described in detail in the following sections. The use of sections is not meant to limit the invention. Each section can apply to any aspect of the invention. The invention is not limited to the particular component parts of the compositions described or process steps of the methods described as such compositions and methods may vary. It is also to be understood that the terminology used herein is for purposes of describing particular embodiments only, and is not intended to be limiting.

As used in the instant specification and the appended claims, the singular forms "a", "an", and "the" include singular and/or plural referents unless the context clearly dictates otherwise. In this application, the use of "or" means "and/or" unless stated otherwise. It is moreover to be understood that, in case parameter ranges are given which are delimited by numeric values, the ranges are deemed to include these limitation values. The disclosures of all of the art cited herein are incorporated by reference in their entireties.

The term "GS Linker", as used herein, relates to a peptide linker that consist predominantly, or exclusively, of Glycin and Serin residues (also called "Gly-Ser linker"). In different embodiments, the GS linker is the linker sown herein in any of SEQ ID NOs: 2, 6 or 8.

A "conservative amino acid substitution", as used herein, has a smaller effect on antibody function than a non-conservative substitution. Although there are many ways to classify amino acids, they are often sorted into six main groups on the basis of their structure and the general chemical characteristics of their R groups.

As used herein, the term "target binding affinity" refers to the affinity of a binding molecule according to the invention, to its target, and is expressed numerically using "KD" values. In general, a higher KD value corresponds to a weaker binding. In some embodiments, the "KD" is measured by a radiolabeled antigen binding assay (MA) or surface plasmon resonance (SPR) assays, using, e.g., a BIAcore™-2000 or a BIAcore™-3000. In certain embodiments, an "on-rate" or "rate of association" or "association rate" or "kon" and an "off-rate" or "rate of dissociation" or "dissociation rate" or "koff" are also determined with the surface plasmon resonance (SPR) technique. In additional embodiments, the "KD", "kon", and "koff" are measured using the Octet® Systems.

As used herein, the term "competes for binding" is used in reference to one of the antibodies defined by the sequences as above, meaning that the actual antibody as an activity which binds to the same target, or target epitope or domain or subdomain, as does said sequence defined antibody, and is a variant of the latter. The efficiency (e.g., kinetics or thermodynamics) of binding may be the same as or greater than or less than the efficiency of the latter. For example, the equilibrium binding constant for binding to the substrate may be different for the two antibodies.

As used herein, the term "maintaining the capability to bind to a given target" means, for example, that the respective variant has a target binding affinity of ≥50% compared to that of the non-modified peptide.

EDB Fibronectin

Fibronectin (UniProt: P02751) is a high-molecular weight (~440 kDa) glycoprotein of the extracellular matrix that binds to membrane-spanning receptor proteins called integrins. Similar to integrins, fibronectin binds extracellular matrix components such as collagen, fibrin, and heparan sulfate proteoglycans (e.g. syndecans).

Fibronectin has been implicated in carcinoma development. In lung carcinoma, fibronectin expression is increased, especially in non-small cell lung carcinoma. The adhesion of lung carcinoma cells to fibronectin enhances tumorigenicity and confers resistance to apoptosis-inducing chemotherapeutic agents. Fibronectin may promote lung tumor growth/survival and resistance to therapy, and has been discussed to represent a novel target for the development of new anti-cancer drugs.

Fibronectin exists as a protein dimer, consisting of two nearly identical monomers linked by a pair of disulfide bonds. The fibronectin protein is produced from a single gene, but alternative splicing of its precursor mRNA, produced from a single copy fibronectin gene, occurs at three sites coding for the EDA, EDB and IIICS domains and results in the creation of several isoforms.

Fibronectin isoforms comprising the EDA or EDB domains are known as oncofetal forms due to their importance in embryonic development and their restricted presence in normal adult tissues. These isoforms are also recognized as important markers of angiogenesis, a crucial physiological process in development and required by tumor cells in cancer progression. ED-B fibronectin is expressed in tumor tissues, particularly in breast carcinomas, brain tumors, lymphoma cells, and prostate cancers. Due to its tissue specific expression profile, ED-B fibronectin is an attractive tumor antigen to utilize for treatment targeting.

IL-12

Interleukin-12 is a heterodimeric cytokine with multiple biological effects on the immune system. It is made up of two subunits, p35 and p40, both of which are required for the secretion of the active form of IL-12, p70. Interleukin-12 acts on dendritic cells (DC), leading to increased maturation and antigen presentation, which can allow for the initiation of a T cell response to tumor specific antigens. It also drives the secretion of IL-12 by DCs, creating a positive feedback mechanism to amplify the response. Once a response is initiated, IL-12 plays a fundamental role in directing the immune system towards a Th1 cytokine profile, inducing CD4+ T cells to secrete interferon-gamma (IFN-γ) and leading to a CD8+ cytotoxic T cell response.

IL-12 is also a strong pro-inflammatory cytokine that leads to the secretion of other cytokines including tumor necrosis factor-alpha (TNF-α) which, combined with IFN-γ, is a prerequisite for the development of CD4+ cytotoxic T lymphocytes (CTL). Furthermore, IL-12 can promote the activation of innate immune cells such as macrophages and eosinophils through its induction of IFN-γ and other cytokines. This activation then leads to IL-12 secretion by these cells and further amplification of both the innate and acquired responses. However, high levels of IL-12, and consequently IFN-γ, have also been associated with induction of antagonistic molecules such as IL-10 and the depletion of signaling molecules downstream of IL-12, such as STAT4.

Previous attempts at utilizing IL-12 as a therapeutic agent were unsuccessful as IL-12 showed at best modest anti-tumor effects which were often accompanied by unacceptably toxic side effects, including fever, fatigue, hematological changes, hyperglycemia, and/or organ dysfunction.

"p35" as used herein means a polypeptide that comprises an amino acid sequence having at least eighty percent (80%) identity to the amino acid sequence indicated below:

(SEQ ID NO: 3)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS.

"p40" as used herein means a polypeptide that comprises an amino acid sequence having at least eighty percent (80%) identity to the amino acid sequence indicated below:

(SEQ ID NO: 1)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS.

"IL-12" as used herein means a polypeptide that (i) comprises both:
(a) p35, or a fragment thereof, wherein p35 comprises an amino acid sequence having at least eighty percent (80%) identity to the amino acid sequence indicated below:

(SEQ ID NO: 3)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS and
(b) p40, or a fragment thereof, wherein p40 comprises an amino acid sequence having at least eighty percent (80%) identity to the amino acid sequence indicated below:

(SEQ ID NO: 1)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS and (ii) can activate an IL-12 receptor.

Linkers

In certain embodiments one or more peptide linkers are independently selected from a $(Gly_n\text{-}Ser)_m$ sequence, a $(Gly_n\text{-}Ala)_m$ sequence, or any combination of a $(Gly_n\text{-}Ser)_m/(Gly_n\text{-}Ala)_m$ sequence, wherein each n is independently an integer from 1 to 5 and each m is independently an integer from 0 to 10. In some embodiments a peptide linker is $(Gly_4\text{-}Ser)_m$ wherein m is an integer from 0 to 10. In some embodiments a peptide linker is $(Gly_4\text{-}Ala)_m$ wherein m is an integer from 0 to 10. Examples of linkers include, but are not limited to, certain embodiments one or more linkers include G4S repeats, e.g., the Gly-Ser linker GGGGS (SEQ ID NO:34), or $(GGGGS)_m$ wherein m is a positive integer equal to or greater than 1. For example, m=1, m=2, m=3. m=4, m=5 and m=6, m=7, m=8, m=9 and m=10. In some embodiments, the linker includes multiple repeats of GGGGS (SEQ ID NO:34), including, but is not limited to $(GGGGS)_3$ or $(GGGGS)_4$. In some embodiments, Ser can be replaced with Ala e.g., linkers G/A such as (GGGGA) (SEQ ID NO:35), or (GGGGA)$_m$ wherein m is a positive integer equal to or greater than 1. In some embodiments, the linker includes multiple repeats of GGGGA (SEQ ID NO:35). In other embodiments, a linker includes combinations and multiples of GGGGS (SEQ ID NO: 34), and GGGGA (SEQ ID NO: 35).

In some embodiments a linker comprises the amino acid sequence GGGGSGGGGSGGGGS (SEQ ID NO:2). In some embodiments a linker comprises the amino acid sequence GSADGGSSAGGSDAG (SEQ ID NO:4). In some embodiments a linker comprises the amino acid sequence GSSGG (SEQ ID NO:6). In some embodiments a linker comprises the amino acid sequence SSSSGSSSSGSSSSG (SEQ ID NO:8). In some embodiments a linker comprises the amino acid sequence GGGAKGGGGKAGGGS (SEQ ID NO:9). In some embodiments a linker comprises the amino acid sequence GGGGDGGGGDGGGGS (SEQ ID NO:10). In some embodiments a linker comprises the amino acid sequence GGGGSGGGGSGGGGS (SEQ ID NO:11). In some embodiments a linker comprises the amino acid sequence GGGGSGGGGEGGGGS (SEQ ID NO:12). In some embodiments a linker comprises the amino acid sequence AEAAAKEAAAKEAAAKA (SEQ ID NO:13). In some embodiments a linker comprises the amino acid sequence APAPAPAPAPAP (SEQ ID NO:14). In some embodiments a linker comprises the amino acid sequence APAPAPAPAPAPAP (SEQ ID NO:15).

Anti-EDB Linked IL-12

The present invention provides, among other things, methods and compositions for treating diseases or disorders associated with the expression of EDB-fibronectin, including cancers. Described herein are new compositions and methods which utilize fibronectin as a target to accomplish cancer-directed delivery of IL-12. This approach promises to fully exploit the therapeutic potential of IL-12, while reducing systemic toxicity and increasing the therapeutic window of IL-12.

Although other constructs containing IL-12 and an EDB fibronectin targeting domain have been previously described, the presently disclosed compositions are surprisingly superior.

WO2006/119897, the content of which is incorporated herein by reference, discloses three different molecular formats of IL-12 combined with an EDB fibronectin targeting antibody named "L19".

Figure 7C:
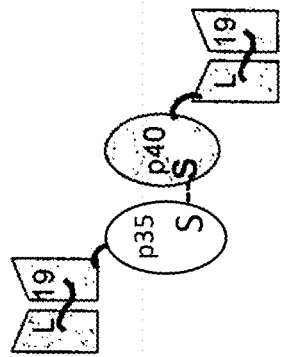
Figure 7B:
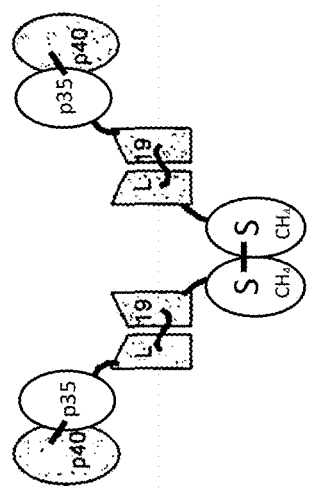
Figure 7A:
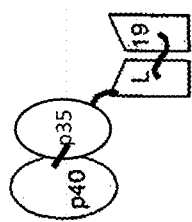

One format was sc(IL-12)-scFv(L19), as illustrated in FIG. 7A. This format, consisting of an IL-12 heterodimer in which the two subunits are joined via a peptide linker (hence, "single chain" IL-12, or sc(IL-12)), and said IL-12 is then joined, via a second peptide linker, to the L19 antibody which is also in the single chain Fv format (hence, scFv(L19)). This format showed modest tumor-targeting ability, consistent with the prior art findings.

Another format was a homodimer of sc(IL-12)-SIP(L19), as illustrated in FIG. 7B. The SIP format ("small immune protein") has been developed by the applicants in WO2003/076469 and is also nicknamed "miniantibody". SIP is a homodimer consisting of two subunits comprising a scFv joined to the CH4 domain. The two CH4 domains are joined to one another by a disulfide bridge. Despite the prior art indication that tumor-targeting properties of L19 could be improved using the SIP format, increased tumor uptake of this conjugate was not observed.

Another format was a heterodimer of IL-12 p40 and p35 subunits joined to one another by a disulfide bridge, and each subunit fused to scFv(L19), forming a scFv(L19)-p35/p40-scFv(L19) heterodimer, as illustrated in FIG. 7C. With this heterodimeric format a marked improvement in tumor uptake of the composition was achieved.

In WO2013/014149, content of which is incorporated herein by reference, the applicant has disclosed two new alternative molecular formats of IL-12 joined to the anti-EDA fibronectin tumor targeting antibody named "F8".

Therein, another format of IL-12 immunoconjugates, comprises a "single chain diabody". It essentially consists of two scFv antibodies with a short—five amino acid-linker (therefore forming a "diabody") joined to one another by a longer—fifteen amino acid-peptide linker.

Figures 8A, 8B, 8C:
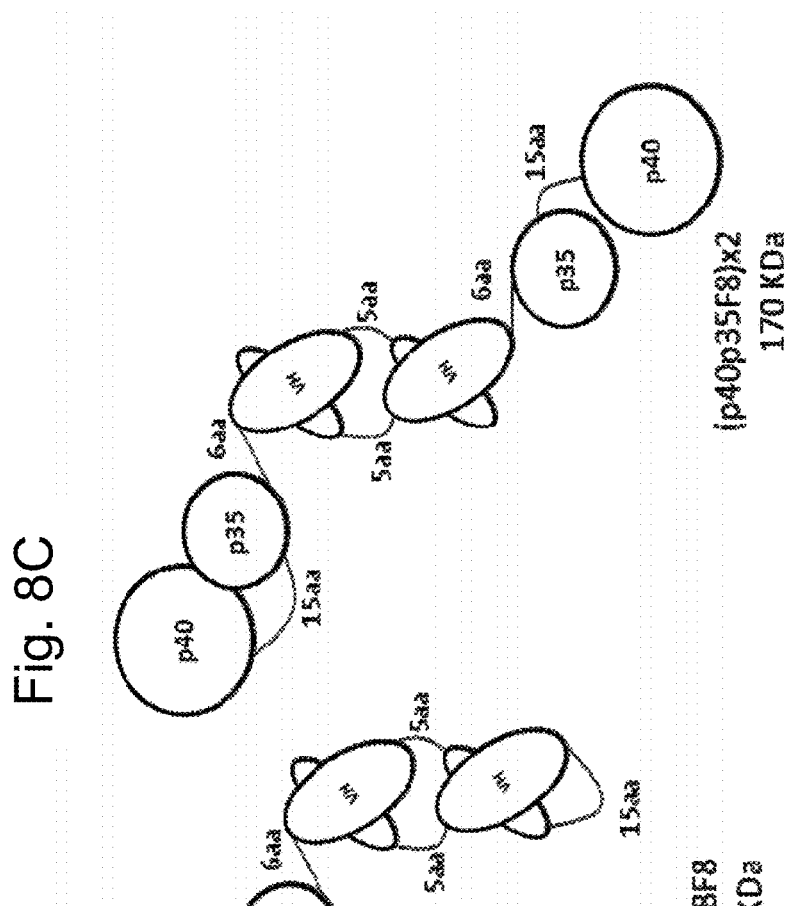
Figure 9A:
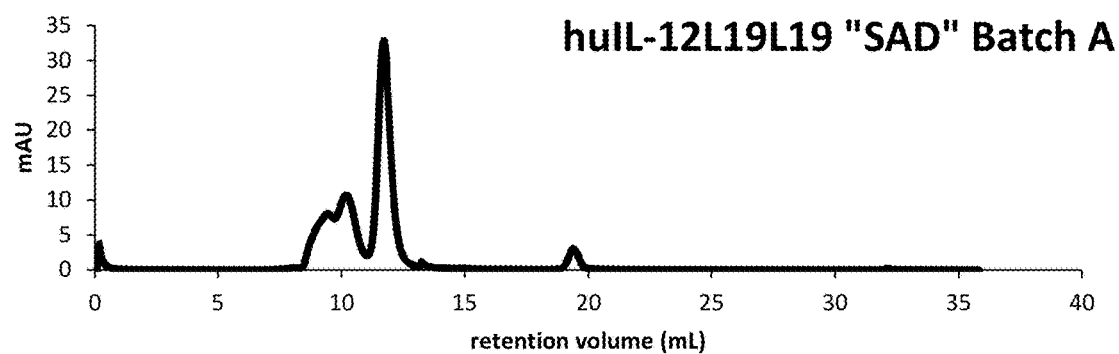
Figure 9B:
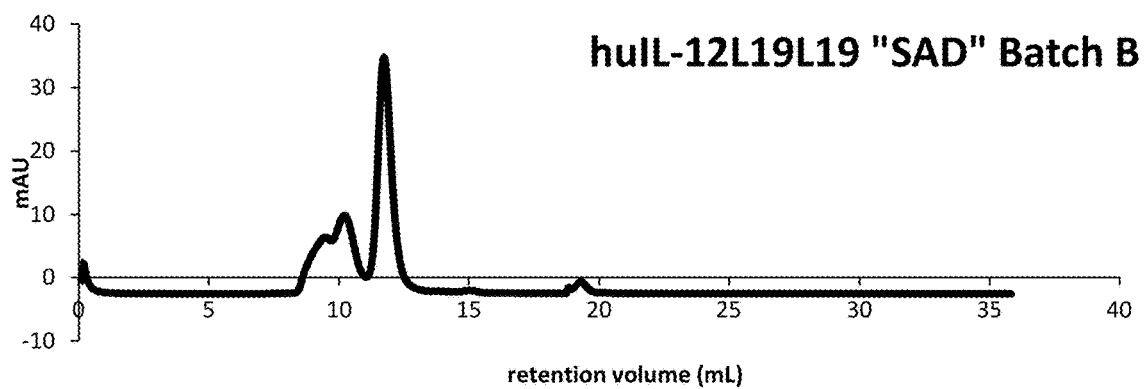
Figure 9C:
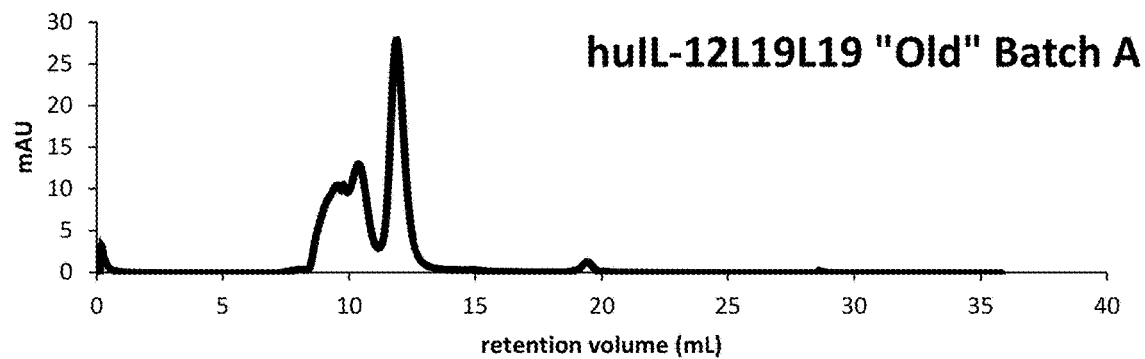
Figure 9D:
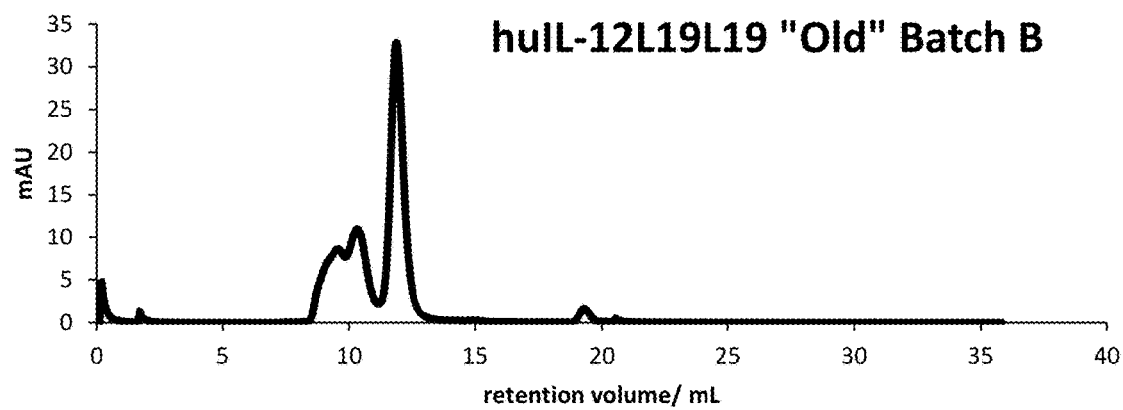

It was shown that a molecular format featuring IL-12 fused to a monospecific F8 single chain diabody (see FIG. 8B) proved to be superior in terms of tumor targeting to either (i) a scFv(F8)-p35/p40-scFv(F8) heterodimer (FIG. 8A) which, in its L19 variant, proved to be the best format disclosed in WO2006/119897 or (ii) two IL-12 molecules joined to a diabody (FIG. 8C).

L19

"L19 antibody" as used herein means any antibody that binds to EDB Fibronectin or any portion thereof and comprises an amino acid sequence having at least seventy-five percent (75%) identity to one or more of the following amino acid sequences:

L19 VH
(SEQ ID NO: 7)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSS

L19 VL
(SEQ ID NO: 5)
EIVLTQSPGTLSLSPGERATLSCRASQSVSSSFLAWYQQKPGQAPRLLIY

YASSRATGIPDRFSGSGSGTDFTLTISRLEPEDFAVYYCQQTGRIPPTFG

QGTKVEIK

CDR1 VH
(SEQ ID NO: 28)
SFSMS

CDR2 VH
(SEQ ID NO: 29)
SISGSSGTTYYADSVKG

CDR3 VH
(SEQ ID NO: 30)
PFPYFDY

CDR1 VL
(SEQ ID NO: 31)
RASQSVSSSFLA

CDR2 VL
(SEQ ID NO: 32)
YASSRAT

CDR3 VL
(SEQ ID NO: 33)
QQTGRIPPT

L19 Diabody
(SEQ ID NO: 36)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSGSSSGGEIVLTQSPGTLSLSPGERATLSCRASQSV

-continued
SSSFLAWYQQKPGQAPRLLIYYASSRATGIPDRFSGSGSGTDFTLTISRL

EPEDFAVYYCQQTGRIPPTFGQGTKVEIK

Pharmaceutical Compositions

A further aspect of the present invention relates to a pharmaceutical composition comprising at least one conjugate of the invention and optionally a pharmaceutically acceptable excipient.

Pharmaceutical compositions of the present invention typically comprise a therapeutically effective amount of a conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients.

The pharmaceutical preparation of the invention may be adapted, for example, for parenteral use and may be administered to the patient in the form of solutions or the like. Compositions comprising the composition of the present invention may be administered to a patient. Administration is preferably in a "therapeutically effective amount", this being sufficient to show benefit to the patient. Such benefit may be at least amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

It is further to be understood that embodiments disclosed herein are not meant to be understood as individual embodiments which would not relate to one another. Features discussed with a particular embodiment are meant to be disclosed also in connection with other embodiments shown herein. If, in one case, a specific feature is not disclosed with one embodiment, but with another, the skilled person would understand that does not necessarily mean that said feature is not meant to be disclosed in combination with said other embodiment. The skilled person would understand that it is the gist of this application to disclose said feature also for the other embodiment, but that just for purposes of clarity and to keep the specification in a manageable volume this has not been done.

Furthermore, the contents of the references referred to herein are incorporated by reference. This refers, particularly, for prior art documents that disclose standard or routine methods. In that case, the incorporation by reference has mainly the purpose to provide sufficient enabling disclosure, and avoid lengthy repetitions.

Generally, the composition of the invention is capable binding to specific target structures in a cell, tissue, organ or patient, which target structures are defined by the specificity of the peptide or protein comprising the EDB binding domain.

Once at the target, IL-12 stimulates the production of IFNγ from T-cells and natural killer cells, and also induces differentiation of Th1 helper cells. IL-12 is a key mediator of innate and cell-mediated immunity. If the peptide or protein comprising the EDB binding domain in the construct is specific for a target structure, e.g., a receptor or an extracellular matrix protein, which characterizes a neoplasticity, e.g., a tumor, a hematologic disease, or cells being in the process of transforming into cancer, the binding of the composition evokes an IL-12 mediated potent anti-cancer and anti-metastatic activity.

The applicants have surprisingly discovered that when a linker comprising an amino acid motif comprising GSADGGSSAGGSDAG is used to link IL-12 to peptide or protein comprising an EDB binding domain (i.e., a diabody as disclosed in WO2013/014149), a better tumor targeting performance as well as a superior production yield can be achieved. At the same time, the binding behaviour of this variant is superior to the binding behaviour of the shorter GSADGG linker, nicknamed herein "Old", and disclosed in WO2013/014149.

The applicants have first evaluated and characterized eight clones of human IL-12 joined to the L19 antibody in single chain diabody format (huIL-12L19L19) with different polypeptide linkers between the cytokine and the L19 single chain diabody.

Five clones nicknamed: (i) "AKKAS" (ii) "DDS" (iii) "(G4S)$_3$" (iv) "SAD" and (v) "SES" contain linkers for conjugation of immunocytokines to recombinant antibodies and have been chosen due to their different electric charge characteristic (neutral, positively charged, negatively charged).

Three additional clones nicknamed (vi) Alpha3 (vii) AP6 and (viii) AP7 were developed. With regards to these three clones, the principles reported in Chen et al (2013) were considered and put into practice. This review suggests that rigid linkers might have a better stability and might maintain the correct distance between the cytokine and the antibody, thus increasing the therapeutic efficacy.

None of the linkers (i)-(viii) were previously tested in this specific immunocytokine.

It was surprisingly found that the "SAD" linker greatly enhances (i) the tumor targeting performance and (ii) the production yield of IL-12 joined to a peptide or protein comprising the EDB binding domain, without (iii) compromising the binding behaviour to ED-B as compared to the other clones. This is quite surprising as despite the consideration of the principles reported by Chen, only the SAD linker resulted in a composition having a number of superior properties when compared to both the "Old" clone (described in more detail below), and the other new variants described herein.

Finally, a ninth clone nicknamed "Old" comprising a linker disclosed in WO2013/014149 was compared to the "SAD" linker. It was surprisingly found that the "SAD" linker despite sharing the first part of the sequence with the "Old" linker has a superior binding affinity to ED-B.

Furthermore, after size-exclusion chromatography, the "SAD" linker shows a higher monomeric portion as compared to the "Old" linker, meaning that assembly of the entire conjugate is more efficient. The higher monomeric portion given by the "SAD" linker would be expected to increase the overall manufacturing yield.

As used herein, the term "single chain diabody" relates to a construct of two single chain Fv (scFv) antibodies with a short linker, preferably 3-10 amino acids long, more preferably 5 amino acid long (also known as "diabodies"), joined to one another by a longer linker, preferably 5-20 amino acids long, more preferably 15 amino acid long, according to the following scheme (N→C orientation): L19VH-linker3-L19VL-linker4-L19VH-linker3-L19VL.

According to some embodiments of the invention, the first subunit of the heterodimeric IL-12 protein is p40 and the second subunit is p35, As discussed above, Fibronectin isoforms comprising the EDA or EDB domains are known as oncofetal forms due to their developmental importance and their re-expression in tumors, contrasting with restricted presence in normal adult tissues.

These isoforms are also recognized as important markers of angiogenesis, a crucial physiological process in development and required by tumor cells in cancer progression.

Hence, the extra-domain B (ED-B) of fibronectin is an attractive target for anti-cancer therapy, including the use of immunocytokines as discussed herein.

According to some embodiments of the invention, the single-chain diabody may comprise an antigen-binding site having the complementarity determining regions (CDRs), or the VH and/or VL domains of an antibody capable of specifically binding to an antigen of interest, for example, one or more CDRs or VH and/or VL domains of an antibody capable of specifically binding to an antigen of the extra-domain B of fibronectin.

An antigen binding site may be provided by means of arrangement of complementarity determining regions (CDRs). The structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. 4$^{th}$ Edition. US Department of Health and Human Services), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, 4$^{th}$ Edition, US Department of Health and Human Services (Kabat et al., (1991a), Sequences of Proteins of Immunological Interest, 5$^{th}$ Edition, US Department of Health and Human Services, Public Service, NIH, Washington, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Thus the single-chain diabody may comprise an antigen-binding site having one, two, three, four, five or six CDR's, or the VH and/or VL domains of antibody L19.

According to some embodiments of the invention, the single-chain diabody may comprise an antigen binding site having the complementarity determining regions (CDRs) of antibody L19 set forth in SEQ ID NOs: 28-33. The antigen binding site may comprise VH and/or VL domains of antibody L19 set forth in SEQ ID NOs: 7 and 5, respectively.

An antigen-binding site may comprise one, two, three, four, five or six CDRs of antibody L19. Amino acid sequences of the CDRs of L19 are:
SEQ ID NO: 28 (VH CDR1);
SEQ ID NO: 29 (VH CDR2);
SEQ ID NO: 30 (VH CDR3);
SEQ ID NO: 31 (VL CDR1);
SEQ ID NO: 32 (VL CDR2), and/or
SEQ ID NO: 33 (VL CDR3).

SEQ ID NOs: 28-30 are the amino acid sequences of the VH CDR regions (1-3, respectively) of the human monoclonal antibody L19. SEQ ID NOs: 31-33 are the amino acid of the VL CDR regions (1-3, respectively) of the human monoclonal antibody L19. The amino acid sequence of the VH and VL domains of antibody L19 correspond to SEQ ID NOs: 7 and 5, respectively.

According to some embodiments of the invention, the single chain diabody comprises at least one of
  a) a set comprising the 3 heavy chain CDRs defined herein as SEQ ID NOs: 28-30, and the 3 light chain CDRs defined herein as SEQ ID NOs: 31-33
  b) a set of 3 heavy chain CDRs in the VH defined herein as SEQ ID NO: 7 and a set of 3 light chain CDRs in the VL defined herein as SEQ ID NO: 5
  c) a heavy chain CDR/light chain CDR combination of a) or b), with the proviso that at least one of the CDRs has up to 3 amino acid substitutions relative to the respective CDR as specified in a) or b), while maintaining its capability to bind to the extra-domain B (ED-B) of fibronectin,
  d) a heavy chain CDR/light chain CDR combination of a) or b), with the proviso that at least one of the CDRs has a sequence identity of ≥66% relative to the respective CDR as specified in a) or b), while maintaining its capability to bind to the extra-domain B (ED-B) of fibronectin,
wherein the CDRs are embedded in a suitable protein framework so as to be capable to bind to the extra-domain B (ED-B) of fibronectin.

In some embodiments, at least one of the CDRs has a sequence identity of ≥67, preferably ≥68, more preferably any one of ≥69, ≥70, ≥71, ≥72, ≥73, ≥74, ≥75, ≥76, ≥77, ≥78, ≥79, ≥80, ≥81, ≥82, ≥83, ≥84, ≥85, ≥86, ≥87, ≥88, ≥89, ≥90, ≥91, ≥92, ≥93, ≥94, ≥95, ≥96, ≥97, ≥98 or most preferably ≥99% sequence identity relative to the respective CDRs.

In another embodiment, at least one of the CDRs has been modified by affinity maturation or other modifications, resulting in a sequence modification compared to the sequences disclosed above.

In some embodiments, at least one of the CDRs has up to 2, and preferably 1 amino acid substitutions relative to the respective CDR as specified in a) or b).

According to some embodiments of the invention, the single chain diabody comprises at least one of
a) a VH and VL domains of antibody L19 set forth in SEQ ID NOs: 7 and 5
b) the heavy chain/light chain variable domain sequence pair of a), with the proviso that at least one of the domains has a sequence identity of ≥80% relative to SEQ ID NO: 7 or SEQ ID NO: 5, respectively and/or
c) the heavy chain/light chain variable domain sequence pair of a), with the proviso that at least one of the domains has up to 10 amino acid substitutions relative to SEQ ID NO: 7, or SEQ ID NO: 5, respectively,
while maintaining its capability to bind to the extra-domain B (ED-B) of fibronectin.

In some embodiments, at least one of the domains has a sequence identity of ≥81, preferably ≥82, more preferably ≥83, ≥84, ≥85, ≥86, ≥87, ≥88, ≥89, ≥90, ≥91, ≥92, ≥93, ≥94, ≥95, ≥96, ≥97, ≥98 or most preferably ≥99% relative to SEQ ID NO: 7, or SEQ ID NO: 5, respectively.

In some embodiments, at least one of the domains has up to 9, preferably up to 8, more preferably up to 7, 6, 5, 4, 3 or 2 and most preferably up to 1 amino acid substitutions relative to SEQ ID NO: 7, or SEQ ID NO: 5, respectively.

According to some embodiments of the invention, at least one amino acid substitution in the single chain diabody is a conservative amino acid substitution.

According to one further embodiment, the composition has the full-length structure "[p40]-[linker1]-[p35]-[SADlinker]-[L19VH]-[linker3]-[L19VL]-[linker4]-[L19VH]-[linker3]-[L19VL]".

According to one further embodiment, the composition has a full-length sequence according to SEQ ID NO: 16.

Disorders

According to a further aspect of the invention, the use of the composition according to the above description (for the manufacture of a medicament) in the treatment of a human or animal subject
being diagnosed for,
suffering from or
being at risk of
developing a neoplastic disease, or for the prevention of such condition, is provided.

According to a further aspect of the invention, the use of the composition according to any of the aforementioned claims (for the manufacture of a medicament) in the inhibition of angiogenesis in a human or animal subject.

Thus, a conjugate as herein described may be used in a method of treating a neoplastic disease or inhibiting angiogenesis by targeting IL-12 to the neovasculature in vivo.

The term "neoplastic disease" encompasses malignant transformations and cancers, including tumors and hematological diseases.

Also contemplated is a method of treating cancer or inhibiting angiogenesis by targeting an agent, in particular a therapeutic agent e.g. IL-12, to the neovasculature in a patient, the method comprising administering a therapeutically effective amount of a conjugate as herein described to the patient. Conditions treatable using the composition as described herein include cancer, other tumors and neoplastic conditions. The composition may be used to inhibit angiogenesis and thereby treat rheumatoid arthritis, diabetic retinopathy, age-related muscular degeneration, angiomas, tumors and cancer. Treatment may include prophylactic treatment. The composition may also be administered in diagnostic methods, e.g. targeting and diagnosis of angiogenesis, which may be associated with any of the above conditions. Other diseases and conditions may also be diagnosed and treated, according to the nature of the protein therapeutic or diagnostic agent contained in the composition, and the specificity of the targeting portion.

Cancers suitable for treatment as described herein include any type of solid or non-solid cancer or malignant lymphoma and especially liver cancer, lymphoma, leukemia (e.g. acute myeloid leukemia), sarcomas, skin cancer, bladder cancer, breast cancer, uterine cancer, ovarian cancer, prostate cancer, lung cancer, colorectal cancer, cervical cancer, head and neck cancer, oesophageal cancer, pancreatic cancer, renal cancer, stomach cancer and cerebral cancer. Cancers may be familial or sporadic. Cancers may be metastatic or non-metastatic.

Preferably, the cancer is a cancer selected from the group of kidney cancer, breast cancer, liver cancer, lung cancer, lymphoma, sarcoma (e.g. gastrointestinal stromal tumor), skin cancer (e.g. melanoma), colorectal cancer, and neuroendocrine tumors.

In some embodiments, the neoplastic disease is characterized by expression or overexpression of ED-B fibronectin.

Compositions of the invention may be administered to a patient in need of treatment via any suitable route, usually by injection into the bloodstream and/or directly into the site to be treated, e.g. tumor or tumor vasculature. The precise dose and its frequency of administration will depend upon a number of factors, the route of treatment, the size and location of the area to be treated (e.g. tumor).

With respect to responsiveness, a subject responds to treatment if a parameter of a cancer (e.g., a hematological cancer, e.g., cancer cell growth, proliferation and/or survival) in the subject is retarded or reduced by a detectable amount, e.g., about 5%, 10%, 20%, 30%, 40%, 50%, 60%, 70%, 80%, 90% or more as determined by any appropriate measure, e.g., by mass, cell count or volume. In one example, a subject responds to treatment if the subject experiences a life expectancy extended by about 5%, 10%, 20%, 30%, 40%, 50% or more beyond the life expectancy predicted if no treatment is administered. In another example, a subject responds to treatment, if the subject has an increased disease-free survival, overall survival or increased time to progression. Several methods can be used to determine if a patient responds to a treatment including, for example, criteria provided by NCCN Clinical Practice Guidelines in Oncology (NCCN Guidelines®).

Combination Therapy

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, ibuprofen or ketoprofen) or opiates such as morphine, or antiemetics.

According to a further aspect of the invention, a combination of the composition or the pharmaceutical composition according to the above description and one or more therapeutically active compounds is provided.

According to a further aspect of the invention, a method for treating or preventing a disorder or condition associated with expression or overexpression of ED-B fibronectin, comprising administering to a subject in need thereof an effective amount of the composition, the pharmaceutical composition or the combination according to the above description is provided.

Kits

According to a further aspect of the invention, a kit of parts comprising:

a) the composition, the pharmaceutical composition or the combination according to the above description,
b) an apparatus for administering the composition, composition or combination, and
c) instructions for use is provided.

In some embodiments, such kit of parts comprises a pre-filled syringe provided with a suitable patient leaflet. In another embodiment, such kit of parts comprises an infusion bottle with suitable user instructions.

The components of a kit are preferably sterile and in sealed vials or other containers.

A kit may further comprise instructions for use of the components in a method described herein. The components of the kit may be comprised or packaged in a container, for example a bag, box, jar, tin or blister pack.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

Example 1

The applicants have surprisingly discovered that when certain linkers are used to join IL-12 to a single-chain diabody (i.e. the superior format disclosed in WO2013/014149), a better tumor targeting performance as well as a superior production yield can be achieved.

The applicants have evaluated and characterized eight clones of human IL-12 joined to the L19 antibody in single chain diabody format (huIL-12L19L19) with different polypeptide linker between the cytokine and the L19 single chain diabody.

Five clones nicknamed: (i) "AKKAS" (ii) "DDS" (iii) "(G4S)₃," (iv) "SAD" and (v) "SES" contain linkers for conjugation of immunocytokines to recombinant antibodies and have been chosen due to their different electric charge characteristic (neutral, positively charged, negatively charged).

Three additional clones nicknamed (vi) Alpha3 (vii) AP6 and (viii) AP7 were developed. With regards to these three clones, the teachings reported in Chen et al (2013) were considered and put into practice. This review suggests that rigid linkers might have a better stability and might maintain the correct distance between the cytokine and the antibody, thus increasing the therapeutic efficacy.

None of the linkers (i)-(viii) were previously tested in this specific immunocytokine.

It was surprisingly found that the "SAD" linker greatly enhances the tumor targeting performance and the production yield of IL-12 joined to a single chain diabody, while being equally capable to bind to ED-B as compared to the other clones.

Materials & Methods

The variants tested in the examples have the following common structure:

| Domain (N->C) | p40 | Linker1 | p35 | Linker2 | L19VH | Linker3 | L19VL | Linker4 | L19VH | Linker3/5 | L19VL |
|---|---|---|---|---|---|---|---|---|---|---|---|
| SEQ ID NO | 1 | 2 | 3 | 4, 9-15 | 7 | 6 | 5 | 8 | 7 | 6 | 5 |

The different variants (also called "clones" herein) differ from one another in the sequence of linker 2, as detailed in Table 2:

TABLE 2

| Linker 2 | SEQ ID NO | Sequence |
|---|---|---|
| AKKAS | 9 | GGGAKGGGGKAGGGS |
| DDS | 10 | GGGGDGGGGDGGGGS |
| (G4S)₃ | 11 | GGGGSGGGGSGGGGS |
| SAD | 4 | GSADGGSSAGGSDAG |
| SES | 12 | GGGGSGGGGEGGGGS |
| Alpha3 | 13 | AEAAAKEAAAKEAAAKA |
| AP6 | 14 | APAPAPAPAPAP |
| AP7 | 15 | APAPAPAPAPAPAP |

Cloning of the Eight Fusion Proteins with Different Linkers

The huIL-12L19L19 coding sequence has been generated by assembling different PCR fragments: the L19 antibody and the IL12 payload. The L19 gene was PCR amplified from a previously generated fusion protein L19-IL2 template using suitable primers. A second L19 gene was PCR amplified with suitable primers.

At the same time, part of the gene of the p35 domain of IL-12 was PCR amplified from a previously generated IL12-based immunocytokine using suitable primers. The two intermediate fragments were PCR-assembled (to generate a P35-L19 fragment), double digested with BamHI/BspEI and cloned into the double digested vector containing a p35. The newly generated p35-L19 vector was subsequently double digested with BspEI/NotI-HF and ligated with a second L19 diabody fragment gene. The fragment p35-L19L19 was digested by BamHI/NotI-HF and cloned into the previously double digested mammalian cell expression vector pcDNA3.1 (+) carrying the p40 subunit gene, resulting in the full length IL12-L19L19.

Different linkers between the IL12 and the single-chain diabody L19 fragments were inserted by means of PCR assembly of fragments "A" (encoding for a part of p35 with the linker), and fragment "B" (encoding for the linker and a part of the antibody). The different fragments "A" and fragments "B" were amplified from IL12-L19L19 as template using suitable primers.

The cloning strategy designed for clone AP7 led to the generation of a mutant clone (named AP6). All PCR products were double digested with BamHI-HF and BspEI restriction enzymes and ligated into a P35-L19L19 pcDNA3.1 plasmid. The resulting plasmids were amplified, double digested with NotI-HF and BamHI-HF restriction enzymes and the insert was sub-cloned into a pcDNA3.1 plasmid containing IL12. Resulting DNA plasmids were amplified and used for cell transfection.

Expression Purification of the Eight Fusion Proteins with Different Linkers

For the production of the various human IL-12 fusions, CHO-S cells in suspension were used. The huIL-12L19L19 variants were expressed using transient gene expression. For 1 ml of production $4 \times 10^6$ CHO-S cells in suspension were centrifuged and resuspended in 1 mL of a medium suitable for CHO-S. 0.625 µg of plasmid DNAs followed by 2.5 µg polyethylene imine (PEI; 1 mg/mL solution in water at pH 7.0) per million cells were then added to the cells and gently mixed. The transfected cultures were incubated in a shaker incubator at 31° C. for 6 days.

Finally, the fusion proteins produced by transient gene expression, were purified from the cell culture medium by protein A affinity chromatography and then dialyzed against PBS.

SDS-PAGE

The correct molecular weight of the fusion proteins was analyzed under reducing and non-reducing conditions by SDS-PAGE 10% and SDS-PAGE 12%.

ELISA

To check the correct binding of the various IL-12 fusions, Elisa plates were coated overnight with 50 ug/ml fibronectin domain 7B89 (see WO2001/062800 A1, the content of which is incorporated herein by reference). The immunocytokines were tested at 10 ug/ml and 1 ug/ml. As secondary reagent, Protein A horseradish peroxidase was used. The assay was developed with BM-Blue POD soluble substrate. The colorimetric reaction was stopped by the addition of 333 mM $H_2SO_4$ and the absorbance was measured at wavelengths 450 nm and 650 nm using a microtiter plate reader.

Size Exclusion Chromatography and Biacore

Size-exclusion chromatography was performed on an ÄKTA FPLC system using the Superdex 200 increase column. Surface plasmon resonance experiments affinity measurements were performed by Biacore X100 instrument with purified huIL-12L19L19 clones on a fibronectin 7B89 domain coated CM5 chip. Samples were injected as serial-dilution, concentration range from 1 µM to 250 nM.

Immunofluorescence

To confirm the ability of the various huIL-12 fusions to bind cancer cells, immunofluorescence was performed onto frozen syngeneic F9 teratocarcinoma specimen cryostat sections (8 um). The tumor slices were fixed by ice-cold acetone (5 min). After fixation, coverslips were washed and blocked with 20% fetal bovine serum in PBS for 45 min. HuIL-12L19L19 clones at concentration 5 µg/ml were added in 2% BSA/PBS solution 1 h at room temperature. Coverslips were then washed twice with PBS and secondary antibody mouse anti-human interleukin-12, final dilution 1:1000 was added in 2% BSA/PBS solution at room temperature for 1 h. Coverslips were then washed again twice with PBS and tertiary antibody Goat Anti Mouse, final dilution 1:500, was added. DAPI was used to counterstain nuclei.

Radiolabelling and In Vivo Tumor Targeting

To confirm the ability of the various IL-12 fusions to bind in vivo tumor, their targeting ability was evaluated by biodistribution analysis. 100 µg of each IL-12L19L19 clone were radioiodinated with $^{125}I$ and Chloramine T hydrate and purified on a PD10 column. Radiolabeled proteins were injected into the lateral tail vein of immunocompetent mice bearing s.c. implanted F9 murine teratocarcinoma. Injected dose per mouse varied between 4 and 9 µg. Mice were sacrificed 24 h after injection. Organs were weighed and radioactivity was counted using a Packard Cobra gamma counter. Radioactivity content of representative organs was expressed as the percentage of the injected dose per gram of tissue (% ID/g±standard error).

Results

Cloning, Expression and SDS-PAGE

The eight variants of huIL-12L19L19 fusion proteins were successfully cloned each one with a different polypeptide linker between the cytokine and the L19 single-chain diabody. The SDS-PAGE characterization displayed a molecular weight around 120 kDa for all variants, which confirms the expected protein size (about 109 kDa not glycosylated). The expression yields (by transient gene expression in CHO-S cells) ranged for all variants between 3.5 and 5 mg/L. Surprisingly the clone nicknamed "SAD" showed a yield of 9 mg/L which is remarkably higher than the yield of the other 7 clones. The results are shown in FIGS. 1A-1B.

ELISA

In ELISA, the eight clones Alpha3, AP6, AP7, DDS, SES, AKKAS, (G4S)$_3$ and SAD all confirmed the binding (both at 10 µg/ml and 1 µg/ml concentration) towards the domain 7B89 of human fibronectin. The results are shown in FIG. 2.

BiaCore

A more precise affinity constant determination was performed by Biacore analysis on a domain 7B89 of human fibronectin coated chip (FIG. 3). Samples were injected as serial-dilution, concentration equal to 1000 nM, 750 nM, 500 nM and 250 nM (FIGS. 3A-3B). The apparent KD was estimated by Biacore X100 Evaluation Software.

Size Exclusion Chromatography

The eight clones Alpha3, AP6, AP7, DDS, SES, AKKAS, (G4S)$_3$ and SAD were characterized on size exclusion chromatography (SEC-200 increase), where all clones showed a comparable profile with the major peak corresponding to the monomeric immunocytokine (FIGS. 4A-4B).

Immunofluorescence

An immunofluorescence experiment was performed with the clones Alpha3, AP6, AP7, DDS, SES, AKKAS, (G4S)$_3$ and SAD onto frozen syngeneic F9 teratocarcinoma specimen cryostat section (8 um). All the clones showed a specific binding on the vasculature as compared to the negative control (FIGS. 5A-5C).

In Vivo Tumor Targeting

In vivo targeting was evaluated by biodistribution analysis. The eight clones Alpha3, AP6, AP7, DDS, SES, AKKAS, (G4S)$_3$ and SAD as well as the positive control (the L19 single chain diabody joined to murine IL-12) were radioiodinated with $^{125}I$ and injected (4-9 mg protein/animal) into immunocompetent mice bearing s.c. implanted F9 murine teratocarcinoma. The radioactivity counted 24 hours after the injection, showed an accumulation in the tumor for all the clones, however the "SAD" clone showed a superior accumulation in the tumor as compared to the other seven clones. (FIGS. 6A-6C).

Example 2

In a further set of comparative experiments, it was surprisingly found that the "SAD" linker is also superior to the old (and shorter) GSADGG linker (SEQ ID NO: 26) disclosed in WO2013/014149 in terms of binding capacity, monomeric profile and tumor targeting ability.

Material & Methods

The variants tested in this example have the following common structure:

| Domain (N->C) | p40 | Linker1 | p35 | Linker2 | L19VH | Linker3 | L19VL | Linker4 | L19VH | Linker3/5 | L19VL |
|---|---|---|---|---|---|---|---|---|---|---|---|
| SEQ ID NO | 1 | 2 | 3 | 4, 26 | 7 | 6 | 5 | 8 | 7 | 6 | 5 |

The different variants (also called "clones" herein) differ from one another in the sequence of linker 2:

| Linker 2 | SEQ ID NO | Sequence |
|---|---|---|
| SAD | 4 | GSADGGSSAGGSDAG |
| Old | 26 | GSADGG |

Cloning of Fusion Proteins

Fusion proteins comprising huIL-12 fused via a 6 or 15 amino acids linker, to the L19 antibody in single chain diabody format (namely huIL-12L19L19 "Old", and huIL-12L19L19 "SAD" variants respectively) were cloned along the lines described above.

Expression of Fusion Proteins

Fusion proteins comprising huIL-12 fused via a 6 or 15 amino acids linker, to the L19 antibody in single chain diabody format (namely huIL-12L19L19 "Old", and huIL-12L19L19 "SAD" variants respectively) were produced by transient gene expression in suspension adapted CHO cell cultures. Following transfection cells were maintained in ProCHO-4 medium (supplemented with 4 mM ultraglutamine), for 6 days at 31° C. under shaking conditions, after which the culture supernatant was harvest by centrifugation and further processed to purify the fusion protein.

Purification of Fusion Proteins Using Protein a Resin

Transfected CHO cell suspension cultures were centrifuged for 30 minutes at 5000 rpm at 4° C. The supernatant was further clarified by filtration using 0.45 um filters. Protein A resin was added to the filtered supernatant and the mixture incubated under shaking conditions for ca 1 h. The resin was than collected into a liquid chromatography column, and washed with "buffer A" (100 mM NaCl, 0.5 mM EDTA, 0.1% Tween 20 in PBS pH 7.4) followed by a second wash with "buffer B" (500 mM NaCl 0.5 mM EDTA in PBS pH 7.4). The fusion proteins comprising huIL-12 were eluted by gravity flow using 100 mM TEA. Aliquots were collected and fractions containing the fusion protein, as confirmed by UV spectrometry, were pooled and dialyzed overnight against PBS.

Size Exclusion Chromatography of Fusion Proteins

Size exclusion chromatography of fusion proteins was performed using a Superdex 200 increase 10/300 GL column with PBS as running buffer on a ÄKTA-FPLC system. 100 µl protein solutions were injected into a loop and automatically injected onto the column. UV absorbance at 280 nm was assessed over time. SEC profiles of the fusion proteins were analyzed using the peak integration function of the UNICORN software to quantify the percentage of the monomeric fraction with respect either to the total % area or to the peak % area. To exclude peak artifacts due to sample loading or to salts present in the sample buffers, only the interval between retention volume 5-17.5 mL was considered for quantification.

BIACore

Surface plasmon resonance experiments affinity measurements were performed by BiacoreX100 instrument with the purified "Old" and "SAD" clones on a fibronectin 7B89 domain freshly coated CMS chip. Samples were injected as serial-dilution, concentration equal to 250 nM, 125 nM and 62.5 mM (FIG. 10). The apparent KD was estimated by Biacore X100 Evaluation Software.

Radiolabelling and In Vivo Tumor Targeting

Purified protein samples huIL-12L19L19 "SAD" (with linker GSADGGSSAGGSDAG, SEQ ID NO 4) and huIL-12L19L19 "Old" (with linker GSADGG, SEQ ID NO 26) (100 µg) were radioiodinated with $^{125}$I and Chloramine T hydrate and purified on a PD10 column. Proteins were radioiodinated after Protein A affinity chromatography. Proteins were injected into the lateral tail vein of immunocompetent (129/Sv) mice bearing subcutaneously implanted F9 murine teratocarcinoma. Injected dose per mouse varied between 10 and 11 µg. Mice were sacrificed 24 hours after injection. Organ samples were weighed and radioactivity was counted using a Packard Cobra gamma counter. The protein uptake in the different organs was calculated and expressed as the percentage of the injected dose per gram of tissue (% ID/g±standard error). The protein uptake into the tumor was adjusted by the tumor growth according to Tarli et al. (1999).

Results

Expression and Purification of Fusion Proteins and Size Exclusion Chromatography The two huIL-12L19L19 "SAD", and huIL-12L19L19 "Old" variants were produced by transient gene expression in CHO cells. Experiments were performed in duplicate, where two sets of production experiments were performed on different days giving rise to batches A and B respectively. Following single step purification by Protein-A affinity chromatography, and dialysis versus PBS, homogeneity of protein samples was assessed by size exclusion chromatography (FIGS. 9A-9D). Both protein variants showed a certain degree of protein aggregation as highlighted by the presence of high molecular weight variants eluting at early retention volume. The huIL-12L19L19 "SAD" in both cases showed a better profile as confirmed by quantification of the monomeric portion of the proteins using the peak integration function of the UNICORN software. Indeed, the huIL-12L19L19 "SAD" variant showed lower tendency to aggregation when compared to huIL-12L19L19 "Old", this considering either the monomeric peak area as a percentage of the total area under the curve above the baseline (mean values: 54.57% vs 46.69%, respectively), or the monomeric peak area as a percentage of the sum of all integrated peaks (mean values: 58.83% vs 52.74%, respectively) (Table 1).

TABLE 1

Quantification of the Monomeric fraction of the different fusion proteins assessed by the peak integration function of the UNICORN software.

| Protein | Linker length (amino acids) | Batch | Monomeric Peak Retention Volume (mL) | Monomeric Peak Area/Total Area (*) (%) | Mean Area/Total Area (*) (%) | Monomeric Peak Area/Peak Area (°) (%) | Mean Area/Peak Area (°) (%) |
|---|---|---|---|---|---|---|---|
| huIL-12L19L19 "SAD" | 15 | A | 11.70 | 54.06 | 54.57 | 58.51 | 58.83 |
| huIL-12L19L19 "SAD" | 15 | B | 11.72 | 55.08 |  | 59.14 |  |
| huIL-12L19L19 "Old" | 6 | A | 11.87 | 46.73 | 46.69 | 48.99 | 52.74 |
| huIL-12L19L19 "Old" | 6 | B | 11.86 | 46.65 |  | 56.48 |  |

(*) Peak area as a percent of the total area under the curve above the baseline.
(°) Peak area as a percent of the sum of all integrated peaks.

Biacore

The apparent KD was estimated by Biacore X100 Evaluation Software to be 6.7 nM for the "Old" clone (huIL-12L19L19 "Old" with the linker GSADGG) and 3.8 nM for the "SAD" clone (huIL-12L19L19 "SAD" with the linker GSADGGSSAGGSDAG) (FIG. 10).

In Vivo Tumor Targeting

The radioactivity counted 24 hours after the injection, showed that the "SAD" clone has an unexpectedly superior tumor uptake as compared to the "Old" clone (FIG. 11).

Example 3

The efficacy of the huIL-12L19L19 "SAD" variant is assessed in human patients having malignant melanoma, non-small cell lung cancer (NSCLC), renal cell carcinoma, urothelial carcinoma, head and neck squamous cell carcinoma (HNSCC), microsatellite instability-high (MSI-H) or mismatch repair deficient (dMMR) metastatic colorectal cancer, hepatocellular cancer, gastric cancer, squamous cell carcinoma of the skin, cervical cancer, and diffuse large B-cell lymphoma (DLBCL). At least one cohort of patients demonstrates disease progression on an immune checkpoint blockade therapy-based regimen administered as immediate prior treatment.

Patients receive huIL-12L19L19 "SAD" variant by intravenous administration once-weekly for 8 weeks. Patients receive doses of 4 µg/kg; 8 µg/kg; 12 µg/kg; 16 µg/kg; or 20 µg/kg. Patients are followed for 6 months from the start of treatment, or until withdrawal of consent or progressive disease.

Pharmacokinetic analysis of IL12-L19L19L19-L12 is assessed using sandwich capture of the fusion molecule and the IL12 moiety. Human anti-fusion protein antibodies (HAFA) will be tested by Surface Plasmon Resonance analysis and by sandwich capture. Anti-tumor activity, e.g., efficacy, will be assessed at week 8, week 16 and week 24 using RECIST (version 1.1) for solid tumors or by LUGANO criteria for malignant lymphoma evaluation criteria.

Further Embodiments

According to a first set of embodiments the following is provided:

1. A conjugate comprising
   a) a heterodimeric IL-12 protein having a first and second subunit,
   b) a single chain diabody, and
   c) a linker between the IL-12 protein and the single chain diabody, which linker comprises an amino acid motif comprising SAD 2. The conjugate according to point 1, wherein the SAD linker comprises the amino acid motif GSADGGSSAGGS-DAG (SEQ ID NO: 4)

3. The conjugate according to any of points 1-2, wherein the first subunit of the heterodimeric IL-12 protein is p40 and the second subunit is p35, 4. The conjugate according to any of points 1-3, wherein the single chain diabody is monospecific or bispecific.

5. The conjugate according to any of points 1-4, wherein the single chain diabody binds to the extra-domain B (ED-B) of fibronectin 6. The conjugate according to any of points 1-5, wherein the single chain diabody comprises two L19 VH domains and two L19 VL domains 7. The conjugate according to any of points 1-6, which has the full-length structure [p40]-[linker1]-[p35]-[SAD linker]-[L19VH]-[linker3]-[L19VL]-[linker4]-[L19VH]-[linker3]-[L19VL]

8. The conjugate according to any of points 1-7, which has a full length sequence according to SEQ ID NO: 16

9. Use of the conjugate according to any of the aforementioned points (for the manufacture of a medicament) in the treatment of a human or animal subject
   being diagnosed for,
   suffering from or
   being at risk of
   developing a neoplastic disease, or for the prevention of such condition.

10. Use of the conjugate according to any of the aforementioned points (for the manufacture of a medicament) in the inhibition of angiogenesis in a human or animal subject.

11. A pharmaceutical composition comprising at least the conjugate according to any of points 1-8, and optionally one or more pharmaceutically acceptable excipient.

12. A combination comprising (i) the conjugate according to any one of points 1-8 or the pharmaceutical composition according to point 11 and (ii) one or more therapeutically active compounds.

13. A method for treating or preventing a disorder or condition associated with expression or overexpression of ED-B fibronectin, comprising administering to a subject in need thereof an effective amount of the conjugate according to any one of points 1-8, the pharmaceutical composition according to point 11, or the combination according to point 12.

14. A therapeutic kit of parts comprising:
  a) the conjugate according to any one of points 1-8, the pharmaceutical composition according to point 11 or the combination according to point 12,
  b) an apparatus for administering the conjugate, composition or combination, and
  c) instructions for use.

According to a second set of embodiments the following is provided:

1. A conjugate comprising
  a) a heterodimeric IL-12 protein having a first and second subunit,
  b) a single chain diabody, and
  c) a linker between the IL-12 protein and the single chain diabody, which linker comprises an amino acid motif comprising GSADGGSSAGGSDAG (SEQ ID NO: 4)

2. The conjugate according to any of points 1, wherein the first subunit of the heterodimeric IL-12 protein is p40 and the second subunit is p35, 3. The conjugate according to any of points 1-2, wherein the single chain diabody is monospecific or bispecific.

4. The conjugate according to any of points 1-3, wherein the single chain diabody binds to the extra-domain B (ED-B) of fibronectin 5. The conjugate according to any of points 1-4, wherein the single chain diabody comprises two L19 VH domains and two L19 VL domains 6. The conjugate according to any of points 1-5, which has the full-length structure [p40]-[linker1]-[p35]-[ SAD linker]-[L19VH]-[linker3]-[L19VL]-[linker4]-[L19VH]-[linker3]-[L19VL]

7. The conjugate according to any of points 1-6, which has a full length sequence according to SEQ ID NO: 16

8. Use of the conjugate according to any of the aforementioned points (for the manufacture of a medicament) in the treatment of a human or animal subject
  being diagnosed for,
  suffering from or
  being at risk of
developing a neoplastic disease, or for the prevention of such condition.

9. Use of the conjugate according to any of the aforementioned points (for the manufacture of a medicament) in the inhibition of angiogenesis in a human or animal subject.

10. A pharmaceutical composition comprising at least the conjugate according to any of points 1-7, and optionally one or more pharmaceutically acceptable excipient.

11. A combination comprising (i) the conjugate according to any one of points 1-7 or the pharmaceutical composition according to point 10 and (ii) one or more therapeutically active compounds.

12. A method for treating or preventing a disorder or condition associated with expression or overexpression of ED-B fibronectin, comprising administering to a subject in need thereof an effective amount of the conjugate according to any one of points 1-7, the pharmaceutical composition according to point 10, or the combination according to point 11.

13. A therapeutic kit of parts comprising:
  a) the conjugate according to any one of points 1-7, the pharmaceutical composition according to point 10 or the combination according to point 11,
  b) an apparatus for administering the conjugate, composition or combination, and
  c) instructions for use.

According to a third set of embodiments the following is provided:

1. A conjugate comprising
  a) a heterodimeric IL-12 protein having a first and second subunit,
  b) a single chain diabody, and
  c) a linker between the IL-12 protein and the single chain diabody, which linker comprises an amino acid motif comprising GSADGGSSAGGSDAG (SEQ ID NO: 4)

2. The conjugate according to point 1, wherein the first subunit of the heterodimeric IL-12 protein is p40 and the second subunit is p35.

3. The conjugate according to any one of points 1-2, wherein the single chain diabody is monospecific or bispecific.

4. The conjugate according to any one of points 1-3, wherein the single chain diabody binds to the extra-domain B (ED-B) of fibronectin 5. The conjugate according to any one of the points 1-4, wherein the single chain diabody comprises an antigen-binding site having the complementarity determining regions (CDRs) of antibody L19 set forth in SEQ ID NOs: 28 to 33.

6. The conjugate according to points 1-5, wherein the single chain diabody comprises the VH and VL domains of antibody L19 set forth in SEQ ID NOs: 7 and 5.

7. The conjugate according to any of points 1-6, wherein the single chain diabody comprises at least one of
  a) the heavy chain/light chain variable domain sequence pair of point 6, with the proviso that at least one of the domains has a sequence identity of ≥80% relative to SEQ ID NO: 7 or SEQ ID NO: 5, respectively and/or
  b) the heavy chain/light chain variable domain sequence pair of point 6, with the proviso that at least one of the domains has up to 10 amino acid substitutions relative to SEQ ID NO: 7 or SEQ ID NO: 5, respectively, while maintaining its capability to bind to the extra-domain B (ED-B) of fibronectin.

8. The conjugate according to any one of points 1-7, wherein at least one amino acid substitution in the single chain diabody is a conservative amino acid substitution 9. The conjugate according to any one of points 1-8, wherein the single chain diabody
  has a target binding affinity of ≥50% to the extra-domain B (ED-B) of fibronectin, compared to one of the antibodies of point 5, or point 6, and/or
  competes for binding to bind to the extra-domain B (ED-B) of fibronectin with one of the antibodies of point 5, or point 6.

10. The conjugate according to any one of points 1-9, wherein the single chain diabody comprises two L19 VH domains and two L19 VL domains 11. The conjugate according to any one of points 1-10, which has the full-length structure [p40]-[linker1]-[p35]-[SAD linker]-[L19VH]-[linker3]-[L19VL]-[linker4]-[L19VH]-[linker3]-[L19VL]

12. The conjugate according to any one of points 1-11, which has a full length sequence according to SEQ ID NO: 16

13. Use of the conjugate according to any one of the aforementioned points (for the manufacture of a medicament) in the treatment of a human or animal subject
being diagnosed for,
suffering from or
being at risk of
developing a neoplastic disease, or for the prevention of such condition.

14. Use of the conjugate according to any one of the aforementioned points (for the manufacture of a medicament) for the inhibition of angiogenesis in a human or animal subject.

15. A pharmaceutical composition comprising at least the conjugate according to any one of points 1-12, and optionally one or more pharmaceutically acceptable excipients.

16. A combination comprising (i) the conjugate according to any one of points 1-12 or the pharmaceutical composition according to point 15 and (ii) one or more therapeutically active compounds.

17. A method for treating or preventing a disorder or condition associated with expression or overexpression of ED-B fibronectin, comprising administering to a subject in need thereof an effective amount of the conjugate according to any one of points 1-12, the pharmaceutical composition according to point 15, or the combination according to point 16.

18. A therapeutic kit of parts comprising:
a) the conjugate according to any one of points 1-12, the pharmaceutical composition according to point 15 or the combination according to point 16,
b) an apparatus for administering the conjugate, composition or combination, and
c) instructions for use.

According to one further embodiment of the invention, the SAD linker comprises the amino acid motif GSADGGS-SAGGSDAG (SEQ ID NO: 4). As used herein, the term "single chain diabody" relates to a construct of two single chain Fv (scFv) antibodies with a short linker, preferably 5 amino acid long, conjugated to one another by a longer linker, preferably 15 amino acid long, according to the following scheme (N→C orientation): L19VH-linker3-L19VL-linker4-L19VH-linker3-L19VL.

According to one embodiment of the invention, the linker3 is GSSGG (SEQ ID NO: 6) and the linker$_4$ is SSSSGSSSSGSSSSG (SEQ ID NO: 8). According to one embodiment of the invention, the first subunit of the heterodimeric IL-12 protein is p40 and the second subunit is p35. Preferably, the two subunits are conjugated to one another by a given linker, according to the following scheme (N→C orientation): p40-linker5-p35.

Preferably IL-12 is human IL-12. In a preferred embodiment, the linker1 is GGGGSGGGGSGGGGS (SEQ ID NO: 2). According to one embodiment of the invention, the single chain diabody is monospecific or bispecific. According to one embodiment of the invention, the single chain diabody binds to a splice isoform of fibronectin. According to one embodiment of the invention, the single chain diabody binds to the extra-domain B (ED-B) of fibronectin.

REFERENCES (THE DISCLOSURES OF WHICH ARE HEREIN INCORPORATED BY REFERENCE IN THEIR ENTIRETIES)

Car et al., Toxicologic Pathology (1999), 27(1), 58-63
Chen et al., Adv Drug Deliv Rev. (2013), 65(10), 1357-1369
WO2013/014149
WO2006/119897
Tarli et al., Blood (1999), 94(1), 192-198.

SEQUENCES

The following sequences form part of the disclosure of the present application. A WIPO ST 25 compatible electronic sequence listing is provided with this application, too. For the avoidance of doubt, if discrepancies exist between the sequences in the following table and the electronic sequence listing, the sequences in this table shall be deemed to be the correct ones.

| SEIQ ID NO | qualifier | Sequence |
| --- | --- | --- |
| 1 | P40 | IWELKKDVYVVELDWYPDAPGEMVVLTCDTPEEDGITWTLDQSSEVLGSGKT LTIQVKEFGDAGQYTCHKGGEVLSHSLLLLHKKEDGIWSTDILKDQKEPKNK TFLRCEAKNYSGRFTCWWLTTISTDLTFSVKSSRGSSDPQGVTCGAATLSAE RVRGDNKEYEYSVECQEDSACPAAEESLPIEVMVDAVHKLKYENYTSSFFIR DIIKPDPPKNLQLKPLKNSRQVEVSWEYPDTWSTPHSYFSLTFCVQVQGKSK REKKDRVFTDKTSATVICRKNASISVRAQDRYYSSSWSEWASVPCS |
| 2 | Linker 1 | GGGGSGGGGSGGGGS |
| 3 | P35 | RNLPVATPDPGMFPCLHHSQNLLRAVSNMLQKARQTLEFYPCTSEEIDHEDI TKDKTSTVEACLPLELTKNESCLNSRETSFITNGSCLASRKTSFMMALCLSS IYEDLKMYQVEFKTMNAKLLMDPKRQIFLDQNMLAVIDELMQALNFNSETVP QKSSLEEPDFYKTKIKLCILLHAFRIRAVTIDRVMSYLNAS |
| 4 | Linker 2 ("SAD") | GSADGGSSAGGSDAG |
| 5 | L19VL | EIVLTQSPGTLSLSPGERATLSCRASQSVSSSFLAWYQQKPGQAPRLLIYYA SSRATGIPDRFSGSGSGTDFTLTISRLEPEDFAVYYCQQTGRIPPTFGQGTK VEIK |
| 6 | Linker 3/Linker 5 | GSSGG |
| 7 | L19VH | EVQLLESGGGLVQPGGSLRLSCAASGFTFSSFSMSWVRQAPGKGLEWVSSIS GSSGTTYYADSVKGRFTISRDNSKNTLYLQMNSLRAEDTAVYYCAKPFPYFD YWGQGTLVTVSS |
| 8 | Linker 4 | SSSSGSSSSGSSSSG |

| SEIQ ID NO | qualifier | Sequence |
|---|---|---|
| 9 | Linker 2 ("AKKAS") | GGGAKGGGGKAGGGS |
| 10 | Linker 2 ("DDS") | GGGGDGGGGDGGGGS |
| 11 | Linker 2 ("G4S$_3$") | GGGGSGGGGSGGGGS |
| 12 | Linker 2 ("SES") | GGGGSGGGGEGGGGS |
| 13 | Linker 2 ("Alpha 3") | AEAAAKEAAAKEAAAKA |
| 14 | Linker 2 ("AP6") | APAPAPAPAPAP |
| 15 | Linker 2 ("AP7") | APAPAPAPAPAPAP |
| 16 | Full length SAD variant | IWELKKDVYVVELDWYPDAPGEMVVLTCDTPEEDGITWTLDQSSEVLGSGKT LTIQVKEFGDAGQYTCHKGGEVLSHSLLLLHKKEDGIWSTDILKDQKEPKNK TFLRCEAKNYSGRFTCWWLTTISTDLTFSVKSSRGSSDPQGVTCGAATLSAE RVRGDNKEYEYSVECQEDSACPAAEESLPIEVMVDAVHKLKYENYTSSFFIR DIIKPDPPKNLQLKPLKNSRQVEVSWEYPDTWSTPHSYFSLTFCVQVQGKSK REKKDRVFTDKTSATVICRKNASISVRAQDRYYSSSWSEWASVPCSGGGGSG GGGSGGGGSRNLPVATPDPGMFPCLHHSQNLLRAVSNMLQKARQTLEFYPCT SEEIDHEDITKDKTSTVEACLPLELTKNESCLNSRETSFITNGSCLASRKTS FMMALCLSSIYEDLKMYQVEFKTMNAKLLMDPKRQIFLDQNMLAVIDELMQA LNFNSETVPQKSSLEEPDFYKTKIKLCILLHAFRIRAVTIDRVMSYLNASGS ADGGSSAGGSDAGEVQLLESGGGLVQPGGSLRLSCAASGFTFSSFSMSWVRQ APGKGLEWVSSISGSSGTTYYADSVKGRFTISRDNSKNTLYLQMNSLRAEDT AVYYCAKPFPYFDYWGQGTLVTVSSGSSGGEIVLTQSPGTLSLSPGERATLS CRASQSVSSSFLAWYQQKPGQAPRLLIYYASSRATGIPDRFSGSGSGTDFTL TISRLEPEDFAVYYCQQTGRIPPTFGQGTKVEIKSSSSGSSSSGSSSSGEVQ LLESGGGLVQPGGSLRLSCAASGFTFSSFSMSWVRQAPGKGLEWVSSISGSS GTTYYADSVKGRFTISRDNSKNTLYLQMNSLRAEDTAVYYCAKPFPYFDYWG QGTLVTVSSGSSGGEIVLTQSPGTLSLSPGERATLSCRASQSVSSSFLAWYQ QKPGQAPRLLIYYASSRATGIPDRFSGSGSGTDFTLTISRLEPEDFAVYYCQ QTGRIPPTFGQGTKVEIK |
| 17 | Full length muIL-12-L19-L19 | MWELEKDVYVVEVDWTPDAPGETVNLTCDTPEEDDITWTSDQRHGVIGSGKT LTITVKEFLDAGQYTCHKGGETLSHSLLLLHKKENGIWSTEILKNFKNKTFL KCEAPNYSGRFTCSWLVQRNMDLKFNIKSSSSSPDSRAVTCGMASLSAEKVT LDQRDYEKYSVSCQEDVTCPTAEETLPIELALEARQQNKYENYSTSFFIRDI IKPDPPKNLQMRPLKNSQVEVSWEYPDSWSTPHSYFSLKFFVRIQRKKEKMK ETEEGCNQKGAFLVERTSTEVQCKGGNVCVQAQDRYYNSSCSKWACVPCRVR SGGGGSGGGGSGGGGSRVIPVSGPARCLSQSRNLLKTTDDMVKTAREKLHY SCTAEDIDHEDITRDQTSTLKTCLPLELHKNESCLATRETSSTTRGSCLPPQ KTSLMMTLCLGSIYEDLKMYQTEFQAINAALQNHNHQQIILDKGMLVAIDEL MQSLNHNGETLRQKPPVGEADPYRVKMKLCILLHAFSTRVVTINRVMGYLSS AGSADGEVQLLESGGGLVQPGGSLRLSCAASGFTFSSFSMSWVRQAPGKGLE WVSSISGSSGTTYYADSVKGRFTISRDNSKNTLYLQMNSLRAEDTAVYYCAK PFPYFDYWGQGTLVTVSSGSSGGEIVLTQSPGTLSLSPGERATLSCRASQSV SSSFLAWYQQKPGQAPRLLIYYASSRATGIPDRFSGSGSGTDFTLTISRLEP EDFAVYYCQQTGRIPPTFGQGTKVEIKSSSSGSSSSGSSSSGEVQLLESGGG LVQPGGSLRLSCAASGFTFSSFSMSWVRQAPGKGLEWVSSISGSSGTTYYAD SVKGRFTISRDNSKNTLYLQMNSLRAEDTAVYYCAKPFPYFDYWGQGTLVTV SSGSSGGEIVLTQSPGTLSLSPGERATLSCRASQSVSSSFLAWYQQKPGQAP RLLIYYASSRATGIPDRFSGSGSGTDFTLTISRLEPEDFAVYYCQQTGRIPP TFGQGTKVEIK |
| 18 | AKKAS linker nucleotide sequence | ggaggggggag ctaaaggtgg cggtggcaag caggggggag ggagt |
| 19 | AP7 linker nucleotide sequence | gcaccagcac cagcaccagc accagcacca gcaccagcac ca |
| 20 | DDS linker nucleotide sequence | ggaggtgggg gtgatggtgg gggaggtgac ggcggaggtg ggtct |
| 21 | AP6 linker nucleotide sequence | gcaccagcac cagcaccagc accagcacca gcacca |
| 22 | (G4S)3 linker nucleotide sequence | ggtggaggcg gtcaggcgg aggggttct ggcggtggcg gatcg |
| 23 | SES linker nucleotide sequence | ggtggggggtg gtccggagg cggaggcgaa ggcggaggtg gtcg |
| 24 | Alpha3 linker nucleotide sequence | gcagaagcag cagcaaaaga agcagcagca aagaagcag cagcaaaagc a |

| SEIQ ID NO | qualifier | Sequence |
|---|---|---|
| 25 | SAD linker nucleotide sequence | gggtctgcag acggcggatc atcagctggg ggaagtgacg cagga |
| 26 | Linker 2 ("Old") | GSADGG |
| 27 | Full length "Old" variant | IWELKKDVYVVELDWYPDAPGEMVVLTCDTPEEDGITWTLDQSSEVLGSGKT LTIQVKEFGDAGQYTCHKGGEVLSHSLLLLHKKEDGIWSTDILKDQKEPKNK TFLRCEAKNYSGRFTCWWLTTISTDLTFSVKSSRGSSDPQGVTCGAATLSAE RVRGDNKEYEYSVECQEDSACPAAEESLPIEVMVDAVHKLKYENYTSSFFIR DIIKPDPPKNLQLKPLKNSRQVEVSWEYPDTWSTPHSYFSLTFCVQVQGKSK REKKDRVFTDKTSATVICRKNASISVRAQDRYYSSSWSEWASVPCSGGGGSG GGGSGGGGSRNLPVATPDPGMFPCLHHSQNLLRAVSNMLQKARQTLEFYPCT SEEEIDHEDITKDKTSTVEACLPLELTKNESCLNSRETSFITNGSCLASRKTS FMMALCLSSIYEDLKMYQVEFKTMNAKLLMDPKRQIFLDQNMLAVIDELMQA LNFNSETVPQKSSLEEPDFYKTKIKLCILLHAFRIRAVTIDRVMSYLNASGS ADGGEVQLLESGGGLVQPGGSLRLSCAASGFTFSSFSMSWVRQAPGKGLEWV SSISGSSGTTYYADSVKGRFTISRDNSKNTLYLQMNSLRAEDTAVYYCAKPF PYFDYWGQGTLVTVSSGSSSGGEIVLTQSPGTLSLPGERATLSCRASQSVSS SFLAWYQQKPGQAPRLLIYYASSRATGIPDRFSGSGSGTDFTLTISRLEPED FAVYYCQQTGRIPPTFGQGTKVEIKSSSSGSSSSGSSSSGEVQLLESGGGLV QPGGSLRLSCAASGFTFSSFSMSWVRQAPGKGLEWVSSISGSSGTTYYADSV KGRFTISRDNSKNTLYLQMNSLRAEDTAVYYCAKPFPYFDYWGQGTLVTVSS GSSSGGEIVLTQSPGTLSLPGERATLSCRASQSVSSSFLAWYQQKPGQAPRL LIYYASSRATGIPDRFSGSGSGTDFTLTISRLEPEDFAVYYCQQTGRIPPTF GQGTKVEIK |
| 28 | L19 VH CDR1 | SFSMS |
| 29 | L19 VH CDR2 | SISGSSGTTYYADSVKG |
| 30 | L19 VH CDR3 | PFPYFDY |
| 31 | L19 VL CDR1 | RASQSVSSSFLA |
| 32 | L19 VL CDR2 | YASSRAT |
| 33 | L19 VL CDR3 | QQTGRIPPT |
| 34 | GGGGS linker | GGGGS |
| 35 | GGGGA linker | GGGGA |
| 36 | L19 Diabody | EVQLLESGGGLVQPGGSLRLSCAASGFTFSSFSMSWVRQAPGKGLEWVSSIS GSSGTTYYADSVKGRFTISRDNSKNTLYLQMNSLRAEDTAVYYCAKPFPYFD YWGQGTLVTVSSGSSSGGEIVLTQSPGTLSLPGERATLSCRASQSVSSSFLA WYQQKPGQAPRLLIYYASSRATGIPDRFSGSGSGTDFTLTISRLEPEDFAVY YCQQTGRIPPTFGQGTKVEIK |

What is claimed is:

1. A fusion protein comprising the amino acid sequence of SEQ ID NO: 16.

2. A kit comprising:
    a) the fusion protein according to claim 1;
    b) an apparatus for administering the fusion protein of a); and
    c) written instructions.

3. A pharmaceutical composition comprising the fusion protein composition according to claim 1, and one or more pharmaceutically acceptable excipients.

4. A combination comprising the fusion protein according to claim 1 and one or more therapeutically active compounds.

5. The combination of claim 4, wherein the one or more therapeutically active compounds comprises a chemotherapeutic agent.

6. The combination of claim 4, wherein the one or more therapeutically active compounds comprise one or more pain relief agents.

7. A method of treating a subject in need thereof with a pharmaceutical composition according to claim 3, wherein the subject is suffering from a neoplastic disease expressing extra-domain B (ED-B) fibronectin selected from the group consisting of: malignant melanoma, non-small cell lung cancer (NSCLC), renal cell carcinoma, urothelial carcinoma, head and neck squamous cell carcinoma (HNSCC), microsatellite instability-high (MSI-H) or mismatch repair deficient (dMMR) metastatic colorectal cancer, hepatocellular cancer, gastric cancer, squamous cell carcinoma of the skin, cervical cancer, and diffuse large B-cell lymphoma (DLBCL).

8. A polynucleotide encoding a fusion protein comprising the amino acid sequence of SEQ ID NO: 16.

9. A vector comprising a promoter and the polynucleotide of claim 8.

10. An isolated cell comprising a polynucleotide encoding a fusion protein comprising the amino acid sequence of SEQ ID NO: 16.

11. The isolated cell of claim 10, wherein the cell is a CHO cell.

12. A method of making a fusion protein comprising the amino acid sequence of SEQ ID NO: 16 comprising:
    a) contacting a polynucleotide encoding the fusion protein comprising the amino acid sequence of SEQ ID NO: 16 with an isolated cell;
    b) expressing the polynucleotide in sufficient amounts to produce the fusion protein encoded by the polynucleotide of step a); and
    c) recovering the fusion protein.

13. The method of claim 12, wherein the isolated cell is a Chinese hamster ovary (CHO) cell.

* * * * *